United States Patent
Terashima et al.

(10) Patent No.: US 11,193,172 B2
(45) Date of Patent: Dec. 7, 2021

(54) METHOD FOR PREDICTING PROGNOSIS OF PATIENT WITH CANCER OR INFLAMMATORY DISEASE

(71) Applicants: The University of Tokyo, Tokyo (JP); CHIBA PREFECTURE, Chiba (JP)

(72) Inventors: Yuya Terashima, Tokyo (JP); Kouji Matsushima, Tokyo (JP); Etsuko Toda, Tokyo (JP); Mikiya Otsuji, Tokyo (JP); Meiji Itakura, Chiba (JP)

(73) Assignee: TOKYO UNIVERSITY OF SCIENCE FOUNDATION, Tokyo (JP)

( * ) Notice: Subject to any disclaimer, the term of this patent is extended or adjusted under 35 U.S.C. 154(b) by 1067 days.

(21) Appl. No.: 15/542,267

(22) PCT Filed: Jan. 8, 2016

(86) PCT No.: PCT/JP2016/050555
§ 371 (c)(1),
(2) Date: Jul. 7, 2017

(87) PCT Pub. No.: WO2016/111364
PCT Pub. Date: Jul. 14, 2016

(65) Prior Publication Data
US 2018/0237860 A1 Aug. 23, 2018

(30) Foreign Application Priority Data
Jan. 9, 2015 (JP) ............................. JP2015-003630

(51) Int. Cl.
*C12Q 1/6886* (2018.01)
*C12Q 1/04* (2006.01)
*G01N 33/53* (2006.01)
*C12Q 1/6883* (2018.01)
*G01N 33/68* (2006.01)
*G01N 33/574* (2006.01)
*C12Q 1/02* (2006.01)

(52) U.S. Cl.
CPC .......... *C12Q 1/6886* (2013.01); *C12Q 1/025* (2013.01); *C12Q 1/04* (2013.01); *C12Q 1/6883* (2013.01); *G01N 33/53* (2013.01); *G01N 33/57492* (2013.01); *G01N 33/6863* (2013.01); *C12Q 2600/106* (2013.01); *C12Q 2600/118* (2013.01); *C12Q 2600/158* (2013.01); *G01N 2333/7158* (2013.01); *G01N 2800/52* (2013.01); *G01N 2800/7095* (2013.01)

(58) Field of Classification Search
CPC ........ C12Q 1/6886; C12Q 1/025; C12Q 1/04; C12Q 1/6883; G01N 33/53; G01N 33/57492; G01N 33/6863
USPC ......................................................... 702/19
See application file for complete search history.

(56) References Cited

U.S. PATENT DOCUMENTS 7,759,066 B2    7/2010  Matsushima et al.

FOREIGN PATENT DOCUMENTS

WO    WO 03/070946 A1    8/2003

OTHER PUBLICATIONS

"Paradigm Shift from Chemokines to FROUNT, a Receptor Signal Regulatory Molecule." Gan Kiban Seibutsugaku—Kakushinteki Seeds Ikusei Ni Mukete (Cancer Basic Biology—Towards Cultivation of Innovative Seeds), Nanzando Co., Ltd., 2013, p. 130-136, with English translation.
Esaki et al., "Structural Analyses of the Interaction of Chemokine Receptor CCR2/CCR5 and FROUNT: Novel Therapeutic Target Molecules in Chronic Inflammation," Endocrinology, Diabetology & Metabolism, (2012) vol. 35, No. 6, pp. 500-507, with English translation.
Terashima et al., "Pivotal function for cytoplasmic protein FROUNT in CCR2-mediated monoctye chemotaxis," Nature Immunology (Aug. 2005), vol. 6, No. 8, pp. 827-835.
Toda et al., "FROUNT is a Common Regulator of CCR2 and CCR5 Signaling to Control Directional Migration," The Journal of Immunology (2009), vol. 183, pp. 6387-6394.
Itakura et al., European Respiratory Journal, 2013, vol. 42, Supp. 52, Abstract No. 112.

*Primary Examiner* — Jerry Lin
(74) *Attorney, Agent, or Firm* — Birch, Stewart, Kolasch & Birch, LLP

(57) ABSTRACT

Novel means that enables prediction of prognosis of a patient with cancer or inflammatory disease is disclosed. In the method for prediction of prognosis of a patient with cancer or inflammatory disease according to the present invention, the expression level of the FROUNT gene in a sample collected from the patient is measured. Since FROUNT is a poor prognostic factor, the lower the expression level of the FROUNT gene is, the better the prognosis in the patient is predicted to be. Or, the expression level of the CC chemokine receptor/ligand gene in a sample collected from the patient is measured. Since the CC chemokine receptor/ligand gene such as CCR2 or CCR5 is a good prognostic factor, the higher the expression level of the CC chemokine receptor/ligand gene is, the better the prognosis in the patient is predicted to be.

11 Claims, 5 Drawing Sheets
Specification includes a Sequence Listing.

METHOD FOR PREDICTING PROGNOSIS OF PATIENT WITH CANCER OR INFLAMMATORY DISEASE

TECHNICAL FIELD

The present invention relates to a method for predicting prognosis of a patient with cancer or inflammatory disease.

BACKGROUND ART

FROUNT protein is a cytoplasmic protein that binds to the intracellular C-terminal regions of chemokine receptors CCR2 and CCR5, and positively controls migration signals of macrophages and the like (Patent Document 1, Non-patent Documents 1 and 2). This protein is a novel molecule discovered by the group of the present inventors.

Both CCR2 and CCR5 are known to be involved in cancers and inflammatory diseases, and development of inhibitors for CCR2 and CCR5 has been attempted worldwide aiming at discovery of novel therapeutic agents for these diseases. However, none of these attempts has been successful (Non-patent Documents 3 and 4). The targets of the existing approaches have been the binding between a chemokine CCL2 and a receptor CCR2, the binding between chemokines CCL3 to 5 and a receptor CCR5, and the signal transduction system by P13K and the like functioning downstream of the receptors. Inhibition of binding of FROUNT to the chemokine receptors CCR2 and CCR5 has been expected as a novel drug discovery target (Non-patent Documents 3 and 4).

However, there is no known association between FROUNT protein, CC chemokine receptors such as CCR2 to which FROUNT protein binds, or a ligand thereof, and prognosis of cancer or an inflammatory disease.

PRIOR ART DOCUMENT(S)

Patent Document(s)

Patent Document 1: WO 2003/070946

Non-Patent Document(S)

Non-patent Document 1: Nature Immunology. 6: 827-835, 2005
Non-patent Document 2: Journal of Immunology, 183: 6387-6394, 2009
Non-patent Document 3: Endocrinology, Diabetology & Metabolism, 35(6): 500-507 (2012)
Non-patent Document 4: Gan Kiban Seibutsugaku—Kakushinteki Seeds Ikusei Ni Mukete—(Cancer Basic Biology—Towards Cultivation of Innovative Seeds —), Nanzando Co., Ltd., 2013, p. 130-136

SUMMARY OF THE INVENTION

Problems to be Solved by the Invention

An object of the present invention is to provide novel means that enables prediction of prognosis of a patient with cancer or inflammatory disease. Another object is to provide novel means that enables selection of a patient for whom a chemokine inhibitor or a FROUNT inhibitor is highly effective, or a patient in whom considerable improvement of symptoms by administration of the inhibitor is expected.

Means for Solving the Problems

As a result of intensive analysis on association of expressions of FROUNT and CC chemokine receptors/ligands such as CCR2 with postoperative prognosis in lung cancer patients, the present inventors discovered that a group of patients with high expression of FROUNT showed significantly poorer postoperative prognosis than patients with low expression of FROUNT even though there was no difference in the clinical stage at the time of the operation, and that FROUNT is therefore a poor prognostic factor. The present inventors also discovered that CCR2 and CCR5, and their ligands CCL2 and CCL5, are good prognostic factors. The present inventors further discovered that patients with high expression of CCR2 or CCR5 showed good prognosis even when the poor prognostic factor FROUNT was highly expressed, and that a more accurate prediction of prognosis becomes possible by analyzing expression data and prognostic data from a group of known patients and predetermining a cut-off value for the CC chemokine receptor/ligand. Based on the above-described discoveries, the present invention was completed.

That is, the present invention provides a method for predicting prognosis of a patient with cancer or inflammatory disease, said method comprising measuring the expression level of the FROUNT gene in a sample collected from said patient, wherein the lower the expression level of the FROUNT gene is, the better the prognosis of said patient is predicted to be. The present invention also provides a method for predicting prognosis of a patient with cancer or inflammatory disease, said method comprising measuring the expression level of the CC chemokine receptor/ligand gene in a sample collected from said patient, wherein the higher the expression level of the CC chemokine receptor/ligand gene is, the better the prognosis of said patient is predicted to be, and wherein said CC chemokine receptor/ligand gene is at least one selected from the group consisting of the CCR2 gene, CCR5 gene, CCL2 gene, and the CCL5 gene. The present invention further provides a method for predicting prognosis of a patient with cancer or inflammatory disease, said method comprising measuring the expression level of the FROUNT gene and the expression level of the CC chemokine receptor/ligand gene in a sample collected from said patient, wherein when the expression level of the CC chemokine receptor/ligand gene in said sample is not less than a predetermined reference value, prognosis of said patient is predicted to be good, wherein when the expression level of the CC chemokine receptor/ligand gene in said sample is less than a predetermined reference value, the higher the expression level of the FROUNT gene is, the poorer the prognosis of said patient is predicted to be, and wherein said CC 1.0 chemokine receptor/ligand gene is at least one selected from the group consisting of the CCR2 gene, CCR5 gene, CCL2 gene, and the CCL5 gene.

The present invention still further provides a method for predicting effectiveness of a pharmaceutical comprising as an effective component a FROUNT inhibitor or a chemokine inhibitor, said method comprising measuring the expression level of the FROUNT gene in a sample separated from a patient who is under consideration for administration of said pharmaceutical, wherein the higher the expression level of the FROUNT gene is, the higher the effect of said pharmaceutical in said patient is predicted to be. The present invention still further provides a method for selecting a patient for whom a pharmaceutical comprising as an effective component a FROUNT inhibitor or a chemokine inhibitor is highly effective, said method comprising selecting a patient for whom the pharmaceutical comprising as an effective component a FROUNT inhibitor or a chemokine inhibitor is predicted to be highly effective, wherein said chemokine inhibitor is an inhibitor which inhibits at least one selected from the group consisting of CCR2, CCR5, CCL2, and CCL5. The present invention still further provides a method for selecting a patient for whom administration of a pharmaceutical comprising as an effective component a FROUNT inhibitor or a chemokine inhibitor is desirable, said method comprising investigating expression of the FROUNT gene in a sample collected from a patient, wherein said chemokine inhibitor is an inhibitor which inhibits at least one selected from the group consisting of CCR2, CCR5, CCL2, and CCL5, and wherein a patient in whom expression of the FROUNT gene is detected is selected as a patient for whom administration of the pharmaceutical is desirable.

The present invention still further provides use of a FROUNT gene product as a predictive marker for prognosis showing a negative correlation with prognosis of cancer or inflammatory disease. The present invention still further provides use of a product of at least one gene selected from the group consisting of the CCR2 gene, CCR5 gene, CCL2 gene, and the CCL5 gene, as a predictive marker for prognosis showing a positive correlation with prognosis of cancer or inflammatory disease. The present invention still further provides a kit for prediction of prognosis of cancer or inflammatory disease, said kit comprising at least one of the following (1) and (2):

(1) a primer set, a probe, or an antibody capable of measuring the expression level of the FROUNT gene as a predictive marker for prognosis showing a negative correlation with prognosis of the cancer or inflammatory disease; and (2) a primer set, a probe, or an antibody capable of measuring the expression level of at least one gene selected from the group consisting of the CCR2 gene, CCR5 gene, CCL2 gene, and the CCL5 as a predictive marker for prognosis showing a positive correlation with prognosis of the cancer or inflammatory disease.

Effect of the Invention

The present invention enables prediction of prognosis of a patient with cancer or inflammatory disease based on the expression level of the FROUNT gene as a marker for poor prognosis or the CC chemokine receptor/ligand gene such as CCR2 as a marker for good prognosis. By investigation of the expression levels of both the FROUNT gene and the CC chemokine receptor/ligand gene, the prediction can be carried out more accurately. The result of the prediction of prognosis can be practically used in determination of the course of treatment, follow-up, and the like. Conventionally, various chemokine inhibitors have been studied and developed for the purpose of treatment of cancer and inflammatory diseases. Inhibitors targeting the receptors CCR2 and CCR5, and their ligands CCL2 and CCL5, have also been developed as pharmaceuticals for cancer and inflammatory diseases. Development of inhibitors of FROUNT, which is a novel target molecule for drug discovery, is also being carried out by the group of the present inventors. Pharmaceuticals comprising as an effective component such a chemokine inhibitor or a FROUNT inhibitor are expected to be especially effective for patients in whom the FROUNT gene is highly expressed. The present invention enables prediction of effectiveness of a chemokine inhibitor or a FROUNT inhibitor, and selection of a patient in whom such an inhibitor is highly effective or for whom administration of the inhibitor is desirable.

MODE FOR CARRYING OUT THE INVENTION

Figure 1:
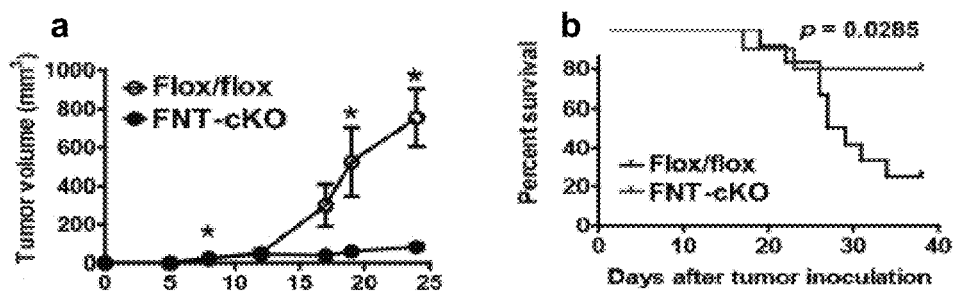
FIG. 1 shows the tumor volume (a) and the survival rate (b) in FROUNT-deficient mice (FNT-cKO) in which FROUNT is conditionally knocked out and non-deficient mice (Flox/flox). Melanoma cells were transplanted to the mice, and the tumor volume and the survival rate were determined.

In the first method of the present invention, the expression level of the FROUNT gene is measured using a sample collected from a patient with cancer or inflammatory disease. The FROUNT gene is a molecule which binds to CCR2 and CCR5 to positively control the migration signals of macrophages and the like, discovered by the group of the present inventors for the first time (Nature Immunology, 6: 827-835. 2005. Journal of Immunology, 183:6387-6394, 2009). Sequence information of the FROUNT gene and FROUNT protein have been deposited in an NCBI database GenBank under Accession Nos. AF498261 and NM 024844. The base sequence and the amino acid sequence deposited under AF498261 are shown in SEQ ID NOs:1 and 2 in SEQUENCE LISTING. Since FROUNT is a poor prognostic factor, the lower the expression level of the FROUNT gene is, the better the prognosis of the patient can be predicted to be. That is, the FROUNT gene product can be utilized as a predictive marker for prognosis showing a negative correlation with prognosis of cancer or inflammatory disease. The term "gene product" includes both mRNA and protein expressed from the gene.

In the second method of the present invention, the expression level of the CC chemokine receptor/ligand gene is measured using a sample collected from a patient with cancer or inflammatory disease. In the present invention, "CC chemokine receptor/ligand gene" is at least one gene selected from the group consisting of the CCR2 gene, CCR5 gene, CCL2 gene, and the CCL5 gene. For example, it may be at least one selected from the CCR2 gene and the CCR5 gene. Or, the CC chemokine receptor/ligand gene may be a combination of the following two genes: the CCR2 gene and the CCL2 gene; or a combination of the following two genes: the CCR5 gene and the CCL5 gene. Since the CC chemokine receptor/ligand is a good prognostic factor, the higher the expression level of the CC chemokine receptor/ligand gene is, the better the prognosis of the patient can be predicted to be. That is, the CC chemokine receptor/ligand gene product can be utilized as a predictive marker for prognosis showing a positive correlation with prognosis of cancer or inflammatory disease. The prognosis is especially good in a patient with high CCR2 expression and high CCL2 expression, and in a patient with high CCR5 expression and high CCL5 gene expression.

There are two isoforms of CCR2, that is, CCR2A and CCR2B, having different C-terminal regions. The major isoform that is widely expressed in cells is CCR2B. The CCR2 to be measured in the present invention is CCR2B. When the term "CCR2" is simply mentioned hereinafter, it means CCR2B unless the context clearly indicates otherwise. The base sequence and the amino acid sequence of CCR2B deposited in GenBank under Accession No. NM_001123396.1 are shown in SEQ ID NOs:3 and 4.

There are two isoforms of CCR5, that is, CCR5A and CCR5B, having different 5'-UTR regions. The sequence of the coding region is the same, and the amino acid sequence of the protein is also the same between these isoforms. When the expression of the CCR5 gene is determined by the expression level of mRNA, both isoforms can be detected by setting primers or the like in the coding region. As a sequence of the CCR5 gene, the base sequence and the amino acid sequence of CCR5A deposited in GenBank under NM_000579.3 are shown in SEQ ID NOs:5 and 6.

The base sequences and the amino acid sequences of CCL2 (NM_002982.3) and CCL5 (NM_002985.2) are shown in SEQ ID NOs:7 to 10, respectively.

In the third method of the present invention, the expression level of the FROUNT gene and the expression level of the CC chemokine receptor/ligand gene are measured using a sample collected from a patient with cancer or inflammatory disease. There is a positive correlation between the expression level of the FROUNT gene and the expression level of the CC chemokine receptor/ligand gene, and a patient with high expression of FROUNT tends to show high expression of the CC chemokine receptor/ligand gene. However, by analysis of data on survival in a known lung cancer patient population, it became clear that a patient in whom the CC chemokine receptor/ligand gene is expressed at a certain level or above shows a good prognosis even though the expression level of FROUNT is high. Accordingly, in the third method, the expression level of the CC chemokine receptor/ligand gene measured in a sample derived from a patient is compared with a reference value of the expression level of the CC chemokine receptor/ligand gene predetermined by analysis of expression data and prognostic data from a known patient population. When the expression level of the CC chemokine receptor/ligand gene in the patient is not less than the reference value, the prognosis of the patient can be predicted to be good.

As described above, a cancer patient in whom the CC chemokine receptor/ligand gene is expressed at a certain level or above shows a good prognosis regardless of high FROUNT expression. In the CC chemokine receptor/ligand high expression group, the ratio of stage I patients is extremely high. Accordingly, when the first method is applied to cancer patients, a patient at stage II or more advanced stage may be selected as a subject whose prognosis is to be predicted. When the first method is carried out on a cancer patient at stage II or more advanced stage, the prediction can also be carried out in a manner where the higher the expression of the FROUNT gene is, the poorer the prognosis is.

The sample to be used for the expression analysis is, for example, a tissue sample of a lesion collected from a patient. In the case of a cancer patient, a lesion tissue sample (microenvironment comprising a cancer cell) can be obtained from a surgical specimen removed by operation. In the case of inflammatory disease, a tissue sample can be obtained from, for example, a biopsy specimen of an inflammatory lesion site (inflammatory microenvironment comprising an inflammatory cell). A tissue piece comprising a cancer cell or an inflammatory cell and a microenvironment-constituting cell in the vicinity thereof may be used. As described later, since values normalized against a standard gene are used as expression level data, it is not necessary to strictly uniformly adjust the weight of the tissue samples even when the expression of mRNA is investigated using RNAs extracted from the tissue samples.

The sample may also be a blood sample or sputum. The most typical example of cells remarkably showing expression of FROUNT among the cells constituting the microenvironments of lesions is macrophages. Since peripheral blood and sputum can reflect the amount of FROUNT-expressing macrophages in the body of a patient, the present invention can also be carried out using a blood sample or sputum.

The method of measurement of the expression level is not limited, and may be any method as long as the expression level can be evaluated quantitatively or semi-quantitatively as numerical data or the like by the method. Examples of the method that may be employed include methods for investigating the expression level of mRNA, such as real-time PCR and Northern blotting; and immunological measurement methods using an antibody against the molecule to be measured, such as Western blotting and immunohistological staining. In the present invention, methods for investigating the expression level of mRNA, especially real-time PCR, may be preferably used. In the present invention, the measured value of the expression level also includes a relative value normalized against a standard gene, and a logarithmic value thereof (log gene expression level). As a standard gene, a housekeeping gene such as the Gapdh gene is usually used.

When the expression level is measured by immunostaining of a tissue sample, the expression level of the molecule to be measured may be quantitatively or semi-quantitatively evaluated based on the degree of staining. The evaluation may be semi-quantitative evaluation by visual observation, or may be quantitative evaluation by digitization of the degree of staining by analysis of a staining image using a computer. When the expression level is evaluated by visual observation of a staining image, whether the expression level is high or not may be evaluated by comparison with a plurality of sample images including low expression cases and high expression cases. In particular, in the first and second methods, the lower or the higher the expression level is, the better the prognosis is predicted to be, and such methods can be carried out without determining a reference value in relation to the expression level. Therefore, in the first and second methods, a method in which the protein expression level is investigated by immunohistological staining or the like may be preferably used besides a method in which the mRNA expression level is investigated. The measurement of the expression level of the FROUNT gene in the third method may be carried out in a similar manner. For example, the third method may be carried out by investigating the protein expression level for FROUNT by e.g. immunohistological staining while investigating the mRNA expression level for the CC chemokine receptor/ligand by e.g. real-time PCR.

The primer set or probe used in the expression analysis such as real-time PCR can be appropriately designed by those skilled in the art based on known sequence information of the FROUNT gene and the CC chemokine receptor/ligand gene (CCR2, CCR5, CCL2, or CCL5). The antibodies for the immunological measurement of FROUNT and the CC chemokine receptor/ligand can also be prepared by those skilled in the art using a well-known conventional method, and appropriate commercially available products may also be used.

In the present invention, the term "expression of a gene" includes both expression of mRNA and expression of protein, and the term "measurement of the expression level of a gene" includes both measurement of expressed mRNA and measurement of expressed protein.

Method for Determination of Reference Value in Third Method

The reference value of the expression level of the CC chemokine receptor/ligand gene can be calculated by statistically analyzing expression data of FROUNT and the CC chemokine receptor/ligand and prognostic data in a known patient population to investigate association between these. In the case of cancer, survival period data (postoperative survival period or disease-free survival period) are commonly used as the prognostic data. In the case of inflammatory disease, data on recurrence, exacerbation, and/or the like are used as the prognostic data. The prognostic data can be obtained as numerical data as appropriate, such as the period before recurrence or exacerbation (the number of days, number of months, or number of years), the total score in evaluation of symptoms during a certain period of time, or the like.

Specific Example 1 of Method for Determination of Reference Value

Expression data and prognostic data in a known patient population are subjected to recursive partitioning analysis to divide the population into a group of poor prognosis patients with high expression of FROUNT (FNT-H), a group of good prognosis patients with low expression of FROUNT (FNT-L), and a group of good prognosis patients with high expression of the CC chemokine receptor/ligand (CC-H). An expression level of the CC chemokine receptor/ligand which distinguishes FNT-H and FNT-L from CC-H can be used as the reference value. For example, when this method is applied to stage I cases (28 cases) in the lung cancer patient population of 68 patients described in the Examples below, the following values are obtained as a reference value, respectively, in terms of the log gene expression level: 1.42 for CCR2; 2.23 for CCR5; and 1.34 for CCL5. Accordingly, for patients with various cancers and inflammatory diseases, preferably for cancer patients, a value between about 1.27 and about 1.57, e.g., between about 1.32 and about 1.52 for CCR2; a value between about 2.08 and about 2.38, e.g., between about 2.13 and about 2.33 for CCR5; and a value between about 1.19 and about 1.49, e.g., between about 1.24 and 7 about 1.44 for CCL5, in terms of the log gene expression level, can be used as a reference value, respectively. However, these values are a mere example, and more desirable values can be obtained by collecting data from more patients. Thus, the scope of the present invention is not limited to such specific values.

Specific Example 2 of Method for Determination of Reference Value

When a patient whose prognosis is to be predicted is a cancer patient, a cut-off value of the expression level of the CC chemokine receptor/ligand gene that significantly distinguishes between a group of known patients at stage I and a group of known patients at stage II or more advanced stage is calculated, and the obtained cut-off value is used as a reference value. Since the concern is whether patients are at stage I (Yes), or stage II or more advanced (No), various statistical analysis methods for binary variables can be employed. Examples of the analysis methods include, but are not limited to, logistic analysis and a support vector machine.

Prediction of Prognosis of Patients Whose Expression Level of CC Chemokine Receptor/Ligand is Less than Reference Value In the case of a patient whose expression level is not more than a reference value, the prediction can be carried out in a manner where the higher the expression level of FROUNT is, the poorer the prognosis is. By determining a reference value by the method of the above-described Specific Example 1, a FROUNT reference value which acts as a cut-off value that distinguishes between the FNT-H group and the FNT-L group can also be obtained. A reference value of the expression level of the CC chemokine receptor/ligand is hereinafter referred to as a CC reference value for the purpose of distinguishing it from a FROUNT reference value. When the expression level of the CC chemokine receptor/ligand in a patient is not more than the CC reference value, the prediction can the carried out as follows: when the FROUNT expression level in the patient is less than a FROUNT reference value, the prognosis is likely to be good, whereas, when the FROUNT expression level in the patient is not less than the reference value, the prognosis is likely to be poor. However, it is indeed a fact that there is a tendency that the higher the expression level of FROUNT is, the poorer the prognosis is.

If the prediction is desired to be carried out more accurately on a patient whose expression level is less than a CC reference value while additionally considering the expression level of the CC chemokine receptor/ligand as a good prognostic factor, a risk index h may be calculated, for example, using the following Equation 1. Each log value is a base-10 logarithm.

$$h = \beta_{CC} \times ([CC] - [CC]_m) + \beta_{FROUNT} \times ([FROUNT] - [FROUNT]_m) \quad \text{Equation 1}$$

In the equation,

[CC] represents a log value of the expression level of the CC chemokine receptor/ligand gene in a sample;

$[CC]_m$ represents a mean or a median of log values of the expression levels of the CC chemokine receptor/ligand gene measured in a known patient population;

[FROUNT] represents a log value of the expression level of the FROUNT gene in a sample;

$[FROUNT]_m$ represents a mean or a median of log values of the expression levels of the FROUNT gene measured in a known patient population;

$\beta_{CC}$ represents a coefficient calculated by applying the Cox proportional hazard model using as a variable log values of the expression levels of the CC chemokine receptor/ligand gene to prognostic data in a known patient population; and $\beta_{FROUNT}$ represents a coefficient calculated by applying the Cox proportional hazard model using as a variable log values of the expression levels of the FROUNT gene to prognostic data in a known patient population.

If h≥0, the prognosis of the patient is predicted to be poor (high risk of poor prognosis), whereas, if h<0, the prognosis of the patient is predicted to be good (low risk of poor prognosis). By carrying out the evaluation such that, for example, h 1.5 indicates a 4.5-fold higher risk (exp(1.5) =4.48), various senses of values of patients and health professionals can be reflected. When the evaluation is carried out as described above, h=0.7 (ln(2)=0.69) corresponds to a 2-fold higher risk, and h=1.1 corresponds to a 3-fold higher risk.

In Equation 1, the log gene expression level normalized against a standard gene such as the Gapdh gene is used as each expression level. Each of $[CC]_m$ and $[FROUNT]_m$ may be the mean or the median.

The coefficients $\beta_{CC}$ and $\beta_{FROUNT}$ may be calculated using all the cases in a known patient population, or may be calculated using cases in whom the expression level of the CC chemokine receptor/ligand gene is less than the CC reference value. In prediction of prognosis of a cancer patient, in addition to the above, the coefficients may also be calculated using cases at stage II or more advanced stage in a known patient population. The following Examples describe specific examples (Equations 1-1 to 1-4) in which each coefficient was calculated by extracting cases at stage II or more advanced stage (40 cases) from a population of 68 lung cancer patients and applying the Cox proportional hazard model thereto. However, the coefficients and the medians employed in the following Equations 1-1 to 1-4 are mere examples, and more desirable coefficients and medians (or means) can be obtained by collecting data from more patient populations. Thus, the scope of the present invention is not limited to these specific values. There are various kinds of known statistical analysis software available for use of the Cox proportional hazard model, and any of such softwares may be used. Those skilled in the art can calculate the coefficients and the medians (or means) in Equation 1 using data from an appropriate patient population and an appropriate kind of statistical analysis software.

Equation 1 is applicable when the expression level in a patient to whom the prediction is to be applied is less than the CC reference value. In the case where the patient is a cancer patient, the accuracy of the prediction is expected to be especially high when the patient is at stage II or more advanced stage and shows an expression level of less than the CC reference value.

The types of the cancers and inflammatory diseases whose prognosis can be predicted by the method of the present invention are not limited, and include various cancers and inflammatory diseases in which at least one of FROUNT, CCR2, CCR5, CCL2, and CCL5 is known to be involved. Cancers and inflammatory diseases in which at least one of CCR2, CCR5, CCL2, and CCL5 is involved are cancers and inflammatory diseases in which FROUNT is involved. Examples of the cancer to be targeted include both solid cancers and humoral cancers. Examples of the cancer 2 to be targeted also include both primary cancers and metastatic cancers.

Specific example of the cancers include, but are not limited to, lung cancer, melanoma, gastric cancer, colon cancer, breast cancer, liver cancer, pancreatic cancer, uterine cancer, esophageal cancer, prostate cancer, malignant lymphoma, and leukemia. Known examples of cancers in which CCR2 is involved include melanoma, breast cancer, prostate cancer, lung cancer, myeloma, and brain tumor, and known examples of cancers in which CCR5 is involved include breast cancer, prostate cancer, lung cancer, pancreatic cancer, and myeloma (Scholten D J, et al., Br J Pharmacol, 165: 1617-1643, 2012). Examples of anticancer drugs in the field of chemokines that have advanced to clinical trials include an anticancer drug for metastatic castration-resistant prostate cancer targeting CCL2, an anticancer drug for non-small cell lung cancer targeting CCL5, an anticancer drug for metastatic cancers targeting CCR2, and an anticancer drug for advanced colon cancer targeting CCR5 (Gan Kiban Seibutsugaku—Kakushinteki Seeds Ikusei Ni Mukete— (Cancer Basic Biology—Towards Cultivation of Innovative Seeds —), Nanzando Co., Ltd., 2013, pp. 130-136). These cancers are preferred specific examples to which the prediction of prognosis according to the present invention is to be applied.

The inflammatory disease to be targeted is typically a chronic inflammatory disease. Specific examples of the inflammatory disease include, but are not limited to, rheumatoid arthritis, fibrosis, peritonitis, multiple sclerosis, arteriosclerosis, diabetes, asthma, Alzheimer's disease, psoriasis, and atopic disease. Examples of inflammatory diseases in which at least one of CCR2, CCR5, CCL2, and CCL5 is known to be involved include arteriosclerosis, multiple sclerosis, rheumatoid arthritis, psoriasis, type 2 diabetes, inflammatory bowel disease, chronic hepatitis, nephritis, graft-versus-host disease, chronic obstructive lung disease, asthma, and acquired immune deficiency syndrome (Scholten D J et al., Br J Pharmacol, 165: 1617-1643, 2012; Clinical Immunology & Allergology, 59(3): 386-391, 2013). Other examples of inflammatory diseases in which at least one of CCR2, CCR5, CCL2, and CCL5, or FROUNT is involved include various fibrotic diseases such as pulmonary fibrosis and hepatic fibrosis; peritonitis; and allergic airway hyperresponsiveness (Nippon Rinsho, vol. 70, extra edition 8, 365-371, 2012; and the Examples described below). These inflammatory diseases are preferred specific examples to which the prediction of prognosis according to the present invention is to be applied.

Conventionally, as described above, various chemokine inhibitors have been studied and developed for the purpose of treatment of cancers and inflammatory diseases. Inhibitors targeting the receptors CCR2 and CCR5, and their ligands CCL2 and CCL5, have also been developed as pharmaceuticals for cancers and inflammatory diseases. An inhibitor of FROUNT, which is a novel target molecule for drug discovery, is also being developed by the group of the present inventors. Pharmaceuticals comprising such a chemokine inhibitor or a FROUNT inhibitor as an effective component are expected to be especially effective for patients in whom the expression level of the FROUNT gene is high. That is, by measuring the expression level of the FROUNT gene in a sample separated from a patient (typically a patient with cancer or a patient with inflammatory disease) who is under consideration for administration of a pharmaceutical comprising as an effective component a FROUNT inhibitor or a chemokine inhibitor which inhibits at least one selected from CCR2, CCR5, CCL2, and CCL5, the effectiveness of the pharmaceutical comprising the above-described inhibitor as an effective component can be predicted. The higher the expression level of the FROUNT gene in the patient is, the higher the effect of the pharmaceutical can be predicted to be. By this method, patients for whom the pharmaceutical comprising the above-described inhibitor as an effective component is highly effective can be selected.

It is thought that, in a patient in whom the expression of FROUNT is not found or is very low, administration of a FROUNT inhibitor or a CC chemokine receptor/ligand inhibitor cannot produce a sufficient effect. On the other hand, in a patient in whom the expression of the FROUNT gene is detected, symptoms are expected to be largely improved by administration of a pharmaceutical comprising the above-described inhibitor as an effective component, and therefore administration of such a pharmaceutical to such a patient is especially desired. That is, by investigating expression of the FROUNT gene in a sample derived from a patient, a patient (typically a patient with cancer or a patient with inflammatory disease) for whom administration of a pharmaceutical comprising the above-described inhibitor as an effective component is desirable can be selected.

A primer set, probe, or antibody capable of measuring the expression level of the FROUNT gene as a predictive marker for prognosis, and a primer set, probe, or antibody capable of measuring the expression level of the CC chemokine receptor/ligand gene as a predictive marker for prognosis may be provided in combination with other reagents, an instruction manual, and/or the like as appropriate as a kit for prediction of prognosis. The kit may comprise either one or both of the primer set, probe, or antibody for measurement of expression of FROUNT and the primer set, probe, or antibody for measurement of expression of the CC chemokine receptor/ligand. In a kit for immunohistological staining, sample staining images including an image of low expression of FROUNT and an image of high expression of FROUNT may also be provided in combination.

EXAMPLES

The present invention is described below more concretely by way of Examples. However, the present invention is not limited to the Examples described below. All animal experiments were carried out in accordance with the guideline of the Animal Care and Use Committee of the University of Tokyo.

1. Hyperplasia and Metastasis of Cancer are Reduced in FROUNT-Deficient Mice

To investigate the role of FROUNT in a tumor microenvironment, mice in which FROUNT was knocked out were prepared using the cre/loxP system. Since complete deficiency of FROUNT causes embryonic lethality, conditional knockout was carried out using a system in which induction of recombination reaction was mediated by tamoxifen.

A targeting vector in which the genomic region containing exons 15 to 19 of the FROUNT gene was sandwiched between LoxP sequences was introduced into mice, and heterozygous $FNT^{flox}$ mice were crossed to create homozygous $FNT^{flox/flox}$ mice. Subsequently, B6.Cg-Tg(CAG-cre/Esr1*)5Amc/J mice (Jaxon Laboratory), in which Cre-ER, a fusion protein of Cre recombinase and a mutant estrogen receptor, was introduced, were crossed with the $FNT^{flox/flox}$ mice to obtain tamoxifen-inducible FROUNT conditional knockout mice FNT-cKO. It could be confirmed that deletion of FROUNT was induced in both the genomic DNA and mRNA by treating the FNT-cKO mice with tamoxifen, and that expression of FROUNT mRNA was suppressed to half or less in the FNT-cKO mice treated with tamoxifen.

When the FNT-cKO mice were used in the experiment, 8- to 16-week-old $FNT^{flox/flox}$ mice and FNT-cKO mice were fed with CE-2 powder feed (CLEA Japan. Inc.) supplemented with tamoxifen citrate (Wako Pure Chemical Industries, Ltd.) in an amount of 0.4 mg/1 g CE-2 from 6 days or 14 days before the experiment to induce expression of Cre, and the recombination was confirmed by Southern blotting.

(1) Reduction of Cancer Hyperplasia in FNT-cKO Mice

To the right abdomen of each of $FNT^{flox/flox}$ mice and FNT-cKO mice, $5 \times 10^5$ B16 melanoma cells were transplanted. Thereafter, the tumor size was measured using a caliper twice a week, and the tumor volume was calculated. The tumor volume was calculated according to the following equation.

$$\text{Tumor volume} = (\text{tumor shorter diameter})^2 \times \text{tumor longer diameter}/2$$

As a result, significant tumor growth inhibition and improved survival rate were observed in FNT-cKO mice compared to non-knockout (FNTflox/flox) mice (FIGS. 1a and 1b).

(2) Reduction of Cancer Metastasis in FNT-cKO Mice

In 200 μL of PBS, $1 \times 10^6$ BI 6F10 melanoma cells were suspended, and the resulting suspension was administered to $FNT^{flox/flox}$ mice and FNT-cKO mice from the tail vein of each mouse. The mice were euthanized on Day 8 post administration, and PBS was perfused from the left ventricle, followed by isolation of lungs. The number and the size of metastatic nodules in the left lobe were visually observed.

Figure 2:
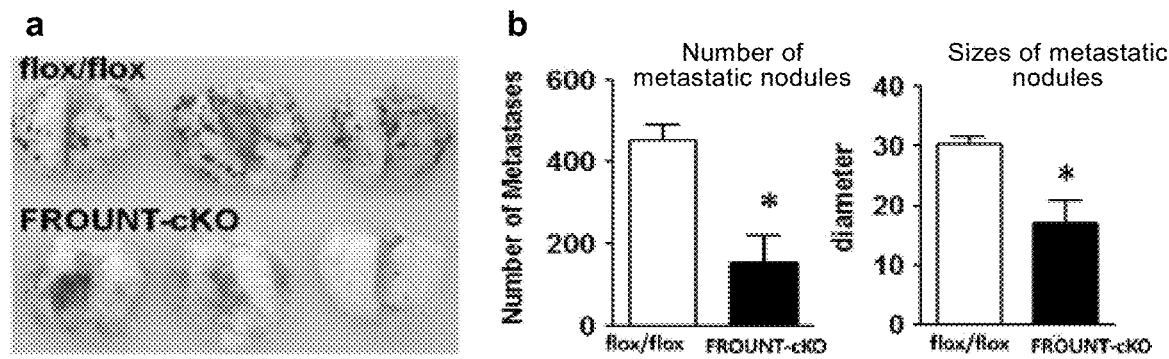
FIG. 2 shows the number and the size of metastatic nodules in lungs investigated in a lung metastasis model of FROUNT-deficient mice (FROUNT-cKO) and non-deficient mice (Flox/flox).

As a result, it became clear that both the number and the size of metastatic nodules were significantly decreased in the FNT-cKO mice (FIGS. 2a and 2b).

2. FROUNT is Highly Expressed in Macrophages

[Methods]

Preparation of FROUNT-Gfp-Knock-in Mice

By a conventional method, FROUNT-gfp knock-in mice were prepared by incorporating a GFP gene downstream of the FROUNT promoter on the mouse genome.

Flow Cytometry

Mice were intraperitoneally injected with 2 mL of 4% thioglycolate to induce peritonitis, and infiltrating cells in the peritoneum were collected from these mice. The cells were washed with PBS supplemented with 2% fetal bovine serum, resuspended, and then filtered through a 70-μm strainer. The Fc receptor was blocked by incubation with an anti-mouse CD16/32 antibody (BD biosciences), and thereafter the cells were stained with a fluorescently labeled antibody. Anti-mouse CD11b-Pacific Blue, anti-mouse Ly6C-APC-Cy7, anti-mouse Ly6G-Alexa Fluor 700, anti-mouse CD4-FITC, and anti-mouse B220-PE-Cy7 were purchased from Biolegend. Anti-mouse CD8-Pacific Blue was purchased from BD biosciences.

[Results]

Figure 3:
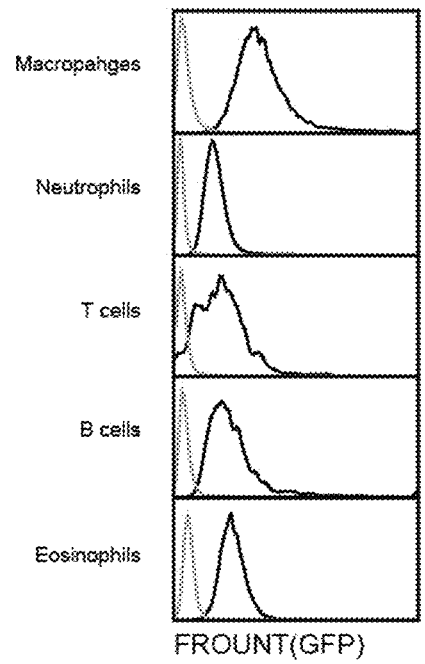
FIG. 3 shows the abundance of each type of cells among cells collected from peritoneal inflammatory sites in wild-type mice and FROUNT-GFP knock-in mice. The abundance was detected by flow cytometry analysis using antibodies against surface markers of various immune cells. Gray curves correspond to cells derived from the wild-type mice, and black curves correspond to cells derived from the GFP knock-in mice.

Flow cytometry analysis of cells derived from the FROUNT-GFP knock-in mice revealed that FROUNT was highly expressed especially in macrophages among the immune cells recruited into the inflammatory sites in the peritonitis model (FIG. 3). It was shown that monocytes/macrophages highly expressing FROUNT were enriched in the cell population mobilized by CCL2, and that FROUNT was highly expressed in cells expressing its receptor CCR2 (data not shown).

3. Accumulation of Macrophages in Tumor Site is Reduced in FROUNT-Deficient Mice

[Methods]

Flow Cytometry

Lung cells of the lung metastasis model of FNT-cKO mice and $FNT^{flox/flox}$ mice described in section 1(2) above were obtained from the right lower lobe by digestion with collagenase and DNase. The cells were washed with PBS supplemented with 2% fetal bovine serum, resuspended, and filtered through a 70-μm strainer. The Fc receptor was blocked by incubation with an anti-mouse CD16/32 antibody (BD biosciences), and thereafter the cells were stained with a fluorescently labeled antibody. Anti-mouse CD11b-Pacific Blue, anti-mouse Ly6C-APC-Cy7, and anti-mouse Ly6G-Alexa Fluor 700 were purchased from Biolegend. The stained cells were analyzed using the Gallios flow cytometer (Beckman coulter).

Immunohistological Staining

Each mouse was perfused with PBS, and the left lung was isolated. Optimal Cutting Temperature Compound (OCT) (Sakura Finetek) was injected from the trachea to embed the lung in OCT, and the lung was then frozen in liquid nitrogen. Fresh frozen sections with a thickness of 8 μm were prepared, and fixed with 4% paraformaldehyde-PBS. After washing with 0.05% Tween 20-PBS, the sections were blocked with Blocking One reagent (Nacalai Tesque), and sequentially stained with an anti-mouse F4/80 antibody (BioLegend) and Alexa Fluor 594 anti-rat IgG (Life technologies). Fluorescence images were obtained with an SP5 confocal microscope (Leica Microsystems).

[Results]

Figure 4:
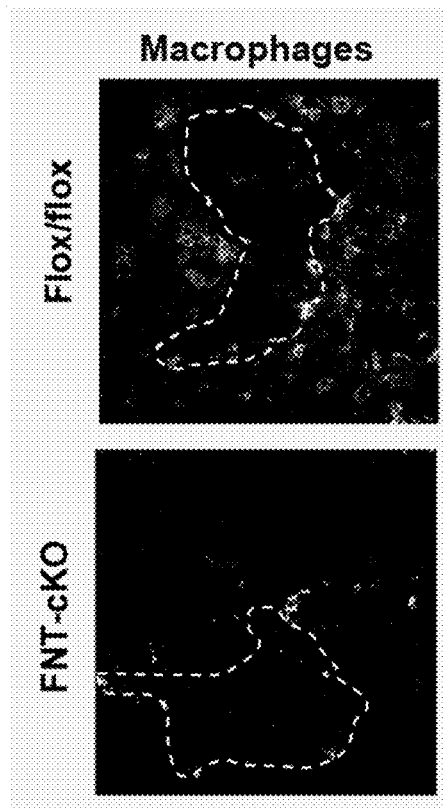
FIG. 4 shows accumulation of macrophages in the vicinity of metastatic nodules in lungs of FROUNT-deficient mice (FROUNT-cKO) and non-deficient mice (Flox/flox) investigated by immunohistological staining. The broken lines in the images indicate the positions of tumor metastatic lesions.

In the FROUNT-deficient FNT-cKO mice, accumulation of macrophages in cancer metastatic nodules was significantly reduced compared to the FROUNT-non-deficient $FNT^{flox/flox}$ mice (FIG. 4).

4. Macrophage Infiltration into Inflammatory Sites is Inhibited in FROUNT-Deficient Mice

[Methods]

In Vivo Chemotaxis Assay

Peritonitis was induced by intraperitoneal administration of 2 mL of 4% thioglycolate medium (Difco) to each of $FNT^{flox/flox}$ mice and FNT-cKO mice. Infiltrating cells in the peritoneum were collected by injecting 5 mL of ice-cold PBS into the abdominal cavity and giving a gentle massage. The collected cells was washed with PBS containing 0.1% FBS, and then subjected to flow cytometry analysis to investigate the cell number and the cell populations.

[Results]

Figure 5:
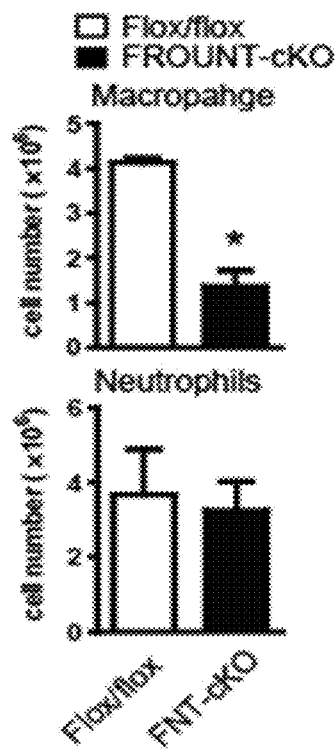
FIG. 5 shows the number of macrophages (upper panel) and the number of neutrophils (lower panel) in cells collected from peritoneal inflammatory sites in FROUNT-deficient mice (FROUNT-cKO) and non-deficient mice (Flox/flox).
Figure 6:
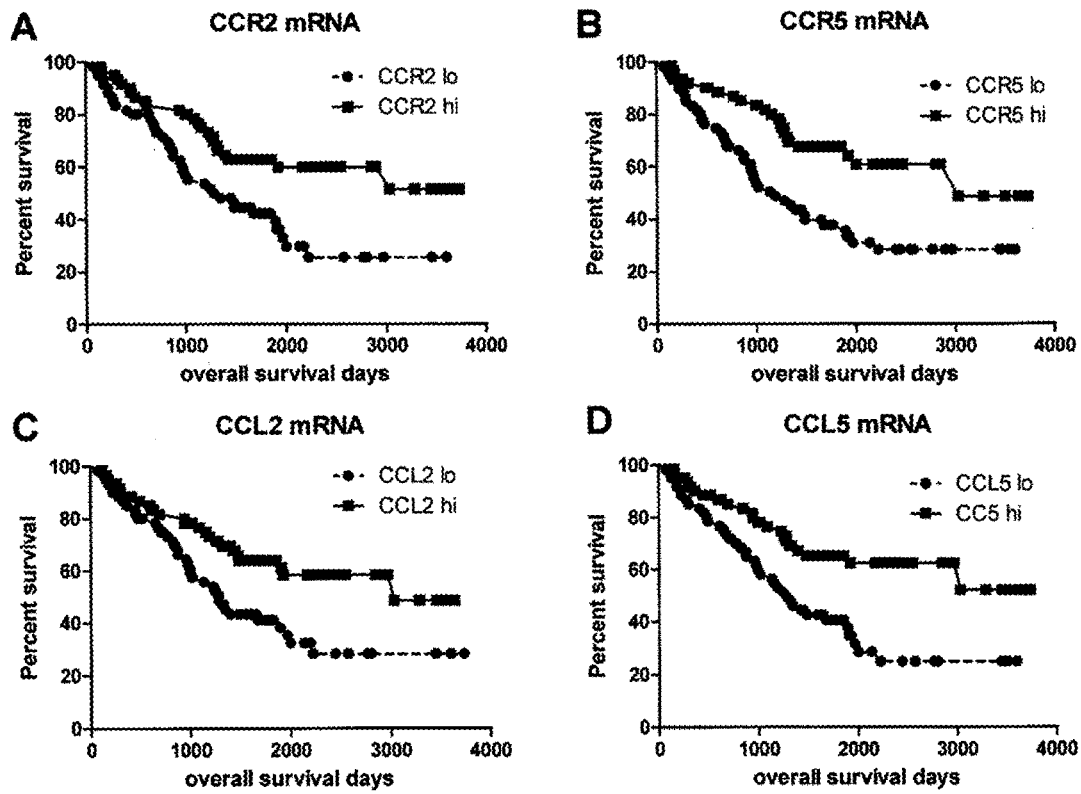
FIG. 6(A) shows a graph of the postoperative survival rates in a CCR2 high expression group and low expression group ($p=0.0038$, $HR=2.11$, 95% CI of ratio 1.27 to 3.50). (B) shows a graph of the postoperative survival rates in a CCR5 high expression group and low expression group ($p=0.0007$, $HR=2.39$, 95% CI of ratio 1.44 to 3.95). (C) shows a graph of the postoperative survival rates in a CCL2 high expression group and low expression group ($p=0.0077$, $HR=1.98$, 95% CI of ratio 1.20 to 3.28). (D) shows a graph of the postoperative survival rates in a CCL5 high expression group and low expression group ($p=0.0014$, $HR=2.27$, 95% CI of ratio 1.37 to 3.76).

The results are shown in FIG. 5. The number of macrophages was decreased in FROUNT-deficient mice, confirming that infiltration of macrophages into peritoneal inflammatory sites was reduced in these mice (FIG. 5, upper panel). No difference was found in the number of neutrophils between the FROUNT-deficient mice and the non-deficient mice, confirming that FROUNT deficiency does not influence infiltration of neutrophils (FIG. 5, lower panel).

5. Association of Expression Level of FROUNT and Expression Levels of CCR2, CCR5, CCL2, and CCL5 with Postoperative Prognosis in Lung Adenocarcinoma Patients <Methods>

Patients

Association of the expression level of FROUNT and the expression levels of CCR2, CCR5, CCL2, and CCL5 with the postoperative prognosis was investigated for 120 patients (52 male patients and 68 female patients) who had undergone lung resection (complete resection of a lung lobe, or segmental resection accompanied by incision of hilar and mediastinal lymph nodes) for lung adenocarcinoma from 1997 to 2004 in Chiba Cancer Center. This research was approved by the institutional review committee and ethics committee in Chiba Cancer Center. Written informed consent was obtained from all patients. Clinical features of the patients are shown in Table 1 below.

TABLE 1

|  | Patients (n = 120) |
|---|---|
| Median age (range) | 67 (44-82) |
| Sex, n (%) | |
| Male | 52 (43.3) |
| Female | 68 (56.7) |
| Stage, n (%) | |
| I | 49 (40.8) |
| II | 20 (16.7) |
| III | 41 (34.2) |
| IV | 10 (8.3) |

Tissue Samples

All tissue samples were frozen in liquid nitrogen immediately after collection, and stored at −80° C. until use. The degree of progression (stage) of cancer was evaluated using the TNM (tumor node metastasis) classification system. The samples were evaluated by two pathologists in Chiba Cancer Center, and further checked by a pathologist specialized in lung pathology.

Quantification of mRNA Level by Real-Time PCR

Total RNA was extracted from the cancer lesion (microenvironment comprising cancer cells) of each surgical specimen using the RNA-Bee reagent (Tel-Test, Inc.) or the TRIzol reagent (Invitrogen) according to the manufacturer's instructions. Using a SuperScript synthesis kit (Life Technologies), cDNA was prepared from 1 µg of the total RNA. The cDNA was amplified using SYBR Green PCR Master Mix (Qiagen), and subjected to real-time quantitative RT-PCR. Each of the forward primer and the reverse primer was used at a final concentration of 0.5 µM in a 20-µL reaction system. The assay was carried out twice using the ABI 7500 real-time PCR system (Life Technologies) according to the manufacturer's instructions. The results were normalized against the RNA expression level of the Gapdh gene. The primers used are shown in Table 2 below.

TABLE 2

| Primer name | Sequence (5'→3') | SEQUENCE LISTING |
|---|---|---|
| FROUNT sense | GCTGCTAAAGATCCAGCCAAT | SEQ ID NO: 11 |
| FROUNT antisense | GATGAGCTCCATTGCTGACA | SEQ ID NO: 12 |
| CCR2 sense | TGAGACAAGCCACAAGCTGA | SEQ ID NO: 13 |
| CCR2 antisense | TTCTGATAAACCGAGAACGAGAT | SEQ ID NO: 14 |
| CCR5 sense | CTAAGCTCAAGGCGTGAGGA | SEQ ID NO: 15 |
| CCR5 antisense | CACTTCCAACCCAAATCCAC | SEQ ID NO: 16 |
| CCL2 sense | TTCTGTGCCTGCTGCTCAT | SEQ ID NO: 17 |
| CCL2 antisense | GGGGCATTGATTGCATCT | SEQ ID NO: 18 |
| CCL5 sense | CCTCATTGCTACTGCCCTCT | SEQ ID NO: 19 |
| CCL5 antisense | GGTGTGGTGTCCGAGGAATA | SEQ ID NO: 20 |
| GAPDH sense | GAAGGTGAAGGTCGGAGTC | SEQ ID NO: 21 |
| GAPDH antisense | GAAGATGGTGATGGGATTTC | SEQ ID NO: 22 |

The expression level was quantitatively analyzed by real-time PCR. The expression level (log gene expression level) of each of FROUNT and chemokine receptors/ligands was calculated according to the following equation.

$$\text{Log gene expression level} = \log_{10} [2^{-(Ct[\text{gene}]-Ct[\text{GAPDH}])}]$$

Ct[gene]: Ct value of FROUNT, CCR2, CCR5, CCL2, or CCL5
Ct[GAPDH]: Ct value of GAPDH
Analysis of Clinical Data Association of the expression level of each of CCR2, CCR5, CCL2, and CCL5 with the prognosis was evaluated by dividing the 120 patients into a high expression group and a low expression group for each gene using the median of the gene expression level as a cut-off value. Significance was tested by the chi-square test. The postoperative survival rate was analyzed by the Kaplan-Meier method (Mantel-Cox test), and the difference between groups was evaluated by the log-rank test. The statistical calculations were carried out using Prism 6 (GraphPad Software). Statistical significance was assumed at $p<0.05$.

Association of the expression level of the FROUNT gene or the CCR2 gene with the postoperative survival rate was evaluated by multivariate Cox proportional hazard analysis. The calculation was carried out using the survival package ("survival" package in R version 3.0.1., Therneau T (2014)._A Package for Survival Analysis in S_. R package version 2.37-7, <URL http://CRAN.R-project.org/package=survival>) in an open-source statistical analysis environment R (R Core Team (2013). R: A language and environment for statistical computing. R Foundation for Statistical Computing, Vienna, Austria. <URL http://www.R-project.org/>). Each result was expressed as a hazard ratio (95% confidence interval). In the same manner as described above, the postoperative survival rate was analyzed by the Kaplan-Meier method (Mantel-Cox test), and the difference between groups was evaluated by the log-rank test. Statistical significance was assumed at $p<0.05$. Recursive partitioning analysis was carried out using the mvpart package ("mvpart" package in R version 3.0.1., rpart by Terry M Therneau, Beth Atkinson. (2014), mvpart: Multivariate partitioning. R package version 1.6-2. <URL http://CRAN.R-project.org/package=mvpart>) of R.

Figure 7:
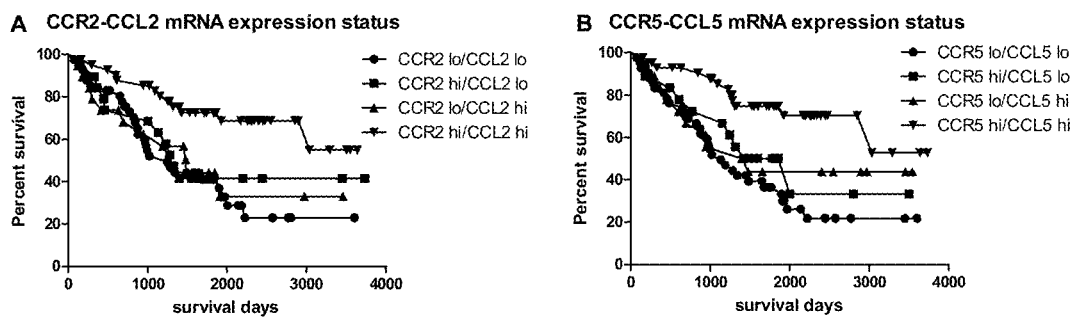
FIG. 7(A) shows a graph showing the relationship between the state of expression of CCR2 and CCL2 and the postoperative survival rate. (B) shows a graph showing the relationship between the state of expression of CCR5 and CCL5 and the postoperative survival rate. "hi" indicates high expression, and "lo" indicates low expression. In both A and B, the group in which both the ligand and the receptor were highly expressed showed a significant difference from other groups ($p<0.05$).

<Results>
High Expression of CCR2, CCR5, CCL2, or CCL5 mRNA is Significant Good Prognostic Factor in Postoperative Course of Lung Adenocarcinoma For evaluation of the prognostic significance of the expression state of the chemokine ligands and receptors (CCR2, CCR5, CCL2, CCL5), the population of 120 patients was divided into a high expression group and a low expression group using the median of the mRNA expression level of each gene as a cut-off value. For any of CCR2, CCR5, CCL2, and CCL5, the prognosis was significantly better in the high expression group than in the low expression group (FIGS. 6A, 6B, 6C, and 6D). The prognosis was especially excellent in the CCR2-high/CCL2-high patient group and the CCR5-high/CCL5-high patient group (FIGS. 7A and 7B).

Expression of FROUNT is Poor Prognostic Factor

Figure 8:
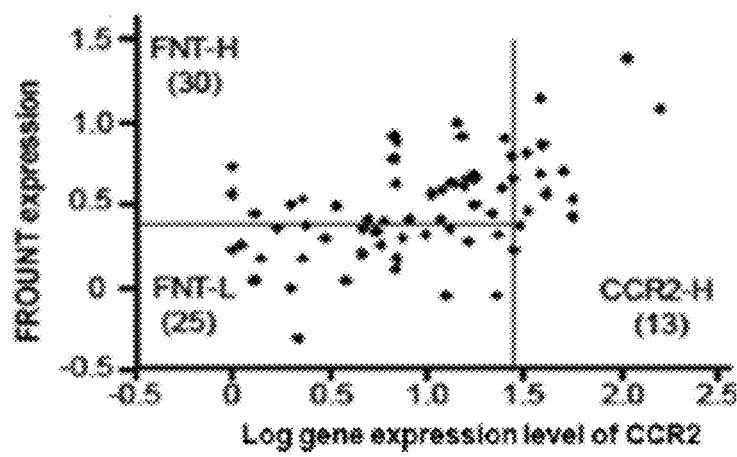
FIG. 8 shows the result obtained by subjecting data on the expression level of FROUNT, the expression level of CCR2, and the postoperative survival period in 68 lung cancer patients to recursive partitioning analysis. The patients were divided into the following three groups: low FROUNT expression (FNT-L), high FROUNT expression (FNT-H), and high CCR2 expression (CCR2-H).

Analysis of gene expression of FROUNT and CCR2 using surgical specimens from 68 female lung cancer patients revealed a positive correlation between expression of FROUNT and expression of CCR2 (FIG. 8 r=0.51, p<0.01). Evaluation of association of the expression levels of FROUNT and CCR2 with the prognosis by multivariate Cox proportional hazard analysis revealed that the hazard ratios for the expression levels of FROUNT and CCR2 were 7.8 (1.8-34, p<0.01) and 0.21 (0.088-0.49, p<0.01), respectively (Table 3). That is, high expression of FROUNT was found to be significantly associated with high mortality risk, and high expression of CCR2 was found to be significantly associated with low mortality risk. In other words, it was revealed that CCR2 is a good prognostic factor (10-fold higher expression corresponds to 0.21-fold risk), and that FROUNT is a poor prognostic factor (10-fold higher expression corresponds to 7.8-fold the risk).

TABLE 3

|  | hazard | lower | upper | p |
|---|---|---|---|---|
| CCR2 | 0.2073 | 0.08802 | 0.4883 | 0.000319 |
| FROUNT | 7.7512 | 1.77128 | 33.9195 | 0.006547 |

Figure 9:
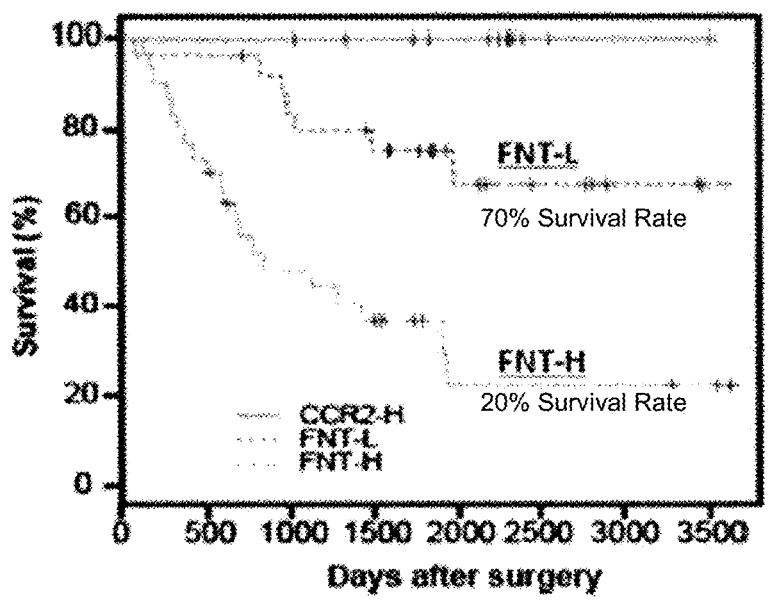
FIG. 9 shows a graph showing the postoperative survival rates in the three patient groups defined by the recursive partitioning analysis. A significant difference was found between the FNT-L group and the FNT-H group ($p<0.05$).
Figure 10:
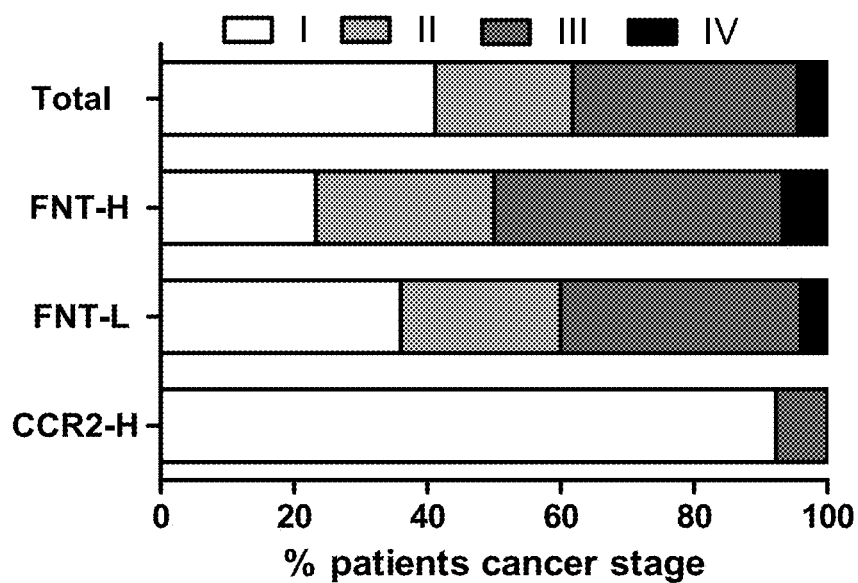
FIG. 10 shows the degrees of progression at the time of operation in 68 lung cancer patients. There was no difference in the degree of progression between the FNT-L group and the FNT-H group. A large proportion of the patients in the CCR2-H group were at stage I.

As a result of dividing of the patients into subgroups by the recursive partitioning algorithm, the patients were divided into the following three patient groups: low FROUNT expression (FNT-L), high FROUNT expression (FNT-H), and high CCR2 expression (CCR2-H) (FIG. 8). Although no difference could be found in the clinical stages between the low FROUNT expression (FNT-L) and the high FROUNT expression (FNT-H) at the time of the operation, the prognosis was found to be better in the low FROUNT expression (FNT-L) than in the high expression (FNT-H) patients according to the Kaplan-Meier and log-rank tests (FIG. 9 and FIG. 10). This result is consistent with the result of the Cox proportional hazard analysis, and thus it was revealed that FROUNT also acts as a poor prognostic factor in patients.

Association of expression of FROUNT and CCR5 with the postoperative prognosis was also evaluated, which resulted in the same results as CCR2 (data not shown).

Study of Threshold of Expression Level of CC Chemokine Receptor/Ligand

The recursive partitioning method was applied to stage I cases (28 cases) among 68 cases to calculate the threshold (reference value) of the expression level of the CC chemokine receptor/ligand. As a result, a value of 1.42 was obtained for CCR2 (that is, the log gene expression level of CCR2 >1.42 indicates good prognosis), a value of 2.23 was obtained for CCR5, and a value of 1.34 was obtained for CCL5. Values within the range of ±0.15, for example, values within the range of ±0.10 or values within the range of ±0.05 of each of these values obtained may be used as a threshold of the expression level of each gene in patients with various cancers and inflammatory diseases, preferably cancer patients.

Study of Prognosis Prediction Equation

The Cox proportional hazard model was applied to the cases at stage II and more advanced stages (40 cases) in a population of 68 lung cancer patients to determine the coefficient for the expression level of each gene in the Equation 1 described above. As for each of $[CC]_m$ and $[FROUNT]_m$, the median in the 40 cases was employed. As a result, the following equations were obtained for the four kinds of CC chemokine receptor/ligand genes, respectively.

$$h=-0.659\times([CCR2]-0.833)+2.44\times([FROUNT]-0.431) \quad \text{Equation 1-1}$$

$$h=-0.385\times([CCR5]-1.69)+2.34\times([FROUNT]-0.431) \quad \text{Equation 1-2}$$

$$h=0.0732\times([CCL2]-0.774)+1.95\times([FROUNT]-0.431) \quad \text{Equation 1-3}$$

$$h=-0.466\times([CCL5]-1.15)+2.33\times([FROUNT]-0.431) \quad \text{Equation 1-4}$$

When the prognosis is predicted based on the expression levels of the CCR2 gene and the FROUNT gene, Equation 1-1 may be used. When the prognosis is predicted based on the expression levels of the CCR5 gene and the FROUNT gene, Equation 1-2 may be used. When the prognosis is predicted based on the expression levels of the CCL2 gene and the FROUNT gene, Equation 1-3 may be used. When the prognosis is predicted based on the expression levels of the CCL5 gene and the FROUNT gene, Equation 1-4 may be used. These equations may be preferably applied, for example, to cases at stage II and more advanced stages, and to cases whose stage are stage I and whose [CC] is less than the reference value.

CONCLUSION

From the above-described analysis results, it was revealed that FROUNT is a key molecule in development/exacerbation of cancers and inflammatory diseases. Quantitative analysis of expression of FROUNT is a novel technique that is useful for diagnosis, monitoring, and prognosis prediction of cancers and inflammatory diseases. It is thought that, among the four CC chemokine receptor/ligand genes, CCR2, CCR5 and CCL5, especially CCR2 and CCR5, can be preferably used as predictive factors for prognosis.

6. Detection of FROUNT-Expressing Macrophages by Immunohistological Staining

[Methods]

Preparation of FROUNT Antibody

The region corresponding to the 23rd to 141st residues of FROUNT protein (SEQ ID NO:2) was expressed in *E. coli* as a recombinant protein, and the recombinant FROUNT protein was purified by a conventional method, followed by immunizing a rabbit with the obtained protein a plurality of times. IgG was purified from sera of the immunized rabbit and a non-immunized rabbit by a conventional method to obtain an anti-FROUNT polyclonal antibody and a control antibody.

Immunohistological Staining

Lung lobes in which a tumor was present were completely removed from lung cancer patients, and hilar and mediastinal lymph nodes were isolated. The surgical specimens were fixed in 10% formalin, and then embedded in paraffin, followed by preparation of sections having a thickness of 4 μm. The sections were immunologically stained using the rabbit anti-FROUNT polyclonal antibody prepared as described above and DAKO Envision FLEX/HRP, and thereafter staining of nuclei was carried out.

[Results]

Figure 11:
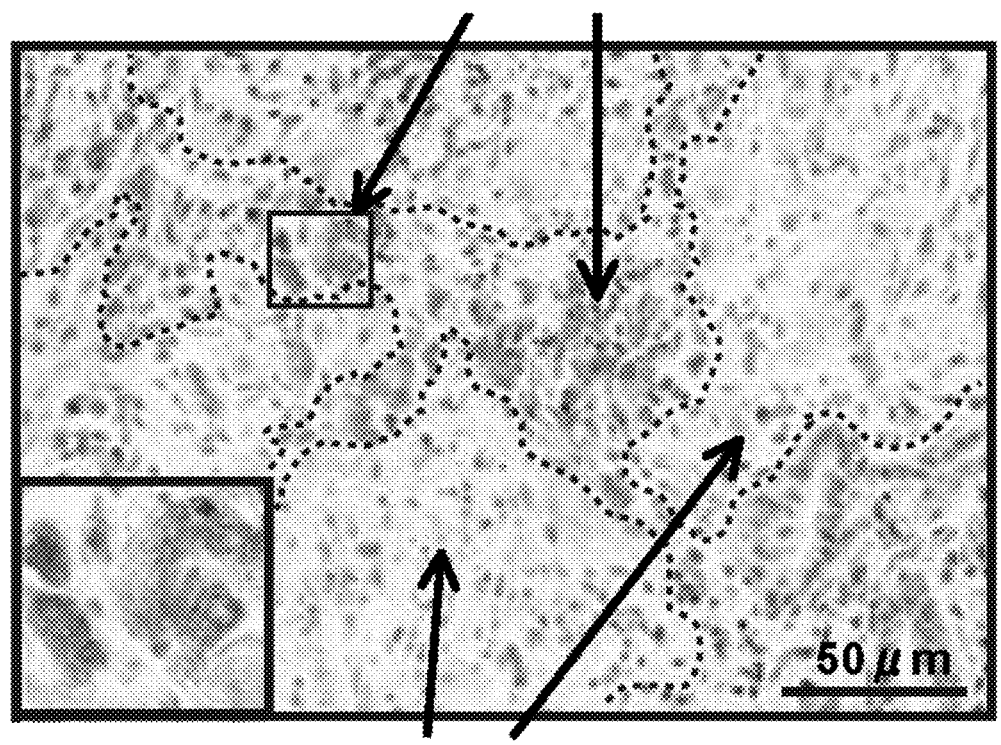
FIG. 11 shows an example of immunohistological staining of surgical 1.5 specimens isolated from lung cancer patients with a FROUNT-specific antibody.

An example of the resulting immunohistological staining images is shown in FIG. 11. Many FROUNT-positive cells, which were stained in brown, could be detected in the vicinities of cancer cell portions. Since the expression level of FROUNT can be evaluated based on the staining intensity and/or the number of stained cells, prediction of prognosis of a patient can be carried out by immunohistological staining of a surgical specimen.

The invention claimed is:

1. A method for predicting prognosis of a patient with cancer or inflammatory disease and treating the patient, said method comprising:
measuring an expression level of FROUNT gene in a sample collected from said patient;
determining prognosis of said patient by determining whether the expression of the FROUNT gene in the sample is detected, wherein a poor prognosis of said patient is indicated when an expression of the FROUNT gene is detected; and
administering an effective amount of a FROUNT inhibitor or a CC chemokine receptor/ligand inhibitor to the patient determined to have a poor prognosis.

2. The method according to claim 1, wherein the measurement of the expression level(s) is carried out by immunohistological staining.

3. The method according to claim 1, which is a method for predicting prognosis of a cancer patient.

4. The method according to claim 1, which is a method for predicting prognosis of a cancer patient at stage II or more advanced stage.

5. The method according to claim 1, wherein said CC chemokine receptor/ligand gene is at least one selected from the group consisting of the CCR2 gene and the CCR5 gene.

6. The method according to claim 1, wherein said sample is a lesion tissue sample.

7. The method according to claim 1, wherein said cancer is lung cancer.

8. A method for predicting prognosis of a patient with cancer or inflammatory disease, said method comprising:
measuring an expression level of FROUNT gene and an expression level of the CC chemokine receptor/ligand gene in a sample collected from said patient, said CC chemokine receptor/ligand gene being at least one selected from the group consisting of the CCR2 gene, CCR5 gene, CCL2 gene, and the CCL5 gene;
comparing the expression level of the CC chemokine receptor/ligand gene measured in said sample with a predetermined CC reference value;
carrying out the following step (i) or (ii):
(i) determining prognosis of said patient as good when the measured expression level is not less than the CC reference value, or
(ii) comparing the expression level of the FROUNT gene measured in said sample with a predetermined FROUNT reference value when the measured expression level of the CC chemokine receptor/ligand gene is less than the predetermined CC reference value, and determining prognosis of said patient as poor if the measured expression level of the FROUNT gene is not less than the FROUNT reference value, or as good if the measured expression level of the FROUNT gene is less than the FROUNT reference value; and
administering an effective amount of a FROUNT inhibitor or a CC chemokine receptor/ligand inhibitor to the patient determined to have a poor prognosis.

9. The method according to claim 8, wherein the measurement of the expression level of the FROUNT gene is carried out by immunohistological staining.

10. The method according to claim 8, wherein said CC reference value and said FROUNT reference value are values calculated by subjecting data on the expression level of the FROUNT gene, data on the expression level of the CC chemokine receptor/ligand gene, and prognostic data in a group of known patients with cancer or inflammatory disease to recursive partitioning analysis.

11. A method for predicting prognosis of a patient with cancer or inflammatory disease, said method comprising:
measuring an expression level of FROUNT gene and an expression level of the CC chemokine receptor/ligand gene in a sample collected from said patient, said CC chemokine receptor/ligand gene being at least one selected from the group consisting of the CCR2 gene, CCR5 gene, CCL2 gene, and the CCL5 gene;
comparing the expression level of the CC chemokine receptor/ligand gene measured in said sample with a predetermined CC reference value;
carrying out the following step (i) or (ii):
(i) determining prognosis of said patient as good when the measured expression level is not less than the CC reference value, or
(ii) applying the measured expression levels of the FROUNT gene and the CC chemokine receptor/ligand gene to the following Equation 1 when the measured expression level is less than the CC reference value, and determining prognosis of said patient as poor if h>0, or as good if h<0; and
administering an effective amount of a FROUNT inhibitor or a CC chemokine receptor/ligand inhibitor to the patient determined to have a poor prognosis:

$$h = \beta_{CC} \times ([CC] - [CC]_m) + \beta_{FROUNT} \times ([FROUNT] - [FROUNT]_m) \quad \text{Equation 1}$$

wherein
$[CC]_m$: a log value of the expression level of the CC chemokine receptor/ligand gene in the sample;
$[CC]_m$: a mean or a median of log values of the expression levels of the CC chemokine receptor/ligand gene measured in a known patient population;
[FROUNT]: a log value of the expression level of the FROUNT gene in the sample;
$[FROUNT]_m$: a mean or a median of log values of the expression levels of the FROUNT gene measured in a known patient population;
βcc: a coefficient calculated by applying the Cox proportional hazard model using as a variable log values of the expression levels of the CC chemokine receptor/ligand gene to prognostic data in a known patient population; and
βFROUNT: a coefficient calculated by applying the Cox proportional hazard model using as a variable log values of the expression levels of the FROUNT gene to prognostic data in a known patient population.

* * * * *

SEQUENCE LISTING

```
<160> NUMBER OF SEQ ID NOS: 22

<210> SEQ ID NO 1
<211> LENGTH: 1971
<212> TYPE: DNA
<213> ORGANISM: Homo sapiens
<220> FEATURE:
<221> NAME/KEY: CDS
<222> LOCATION: (1)..(1971)

<400> SEQUENCE: 1 atg gag gag ctc gat ggc gag cca aca gtc act ttg att cca ggc gtg      48
Met Glu Glu Leu Asp Gly Glu Pro Thr Val Thr Leu Ile Pro Gly Val
```

```
  1              5                  10                 15
aat tcc aag aag aac caa atg tat ttt gac tgg ggt cca ggg gag atg      96
Asn Ser Lys Lys Asn Gln Met Tyr Phe Asp Trp Gly Pro Gly Glu Met
             20                  25                  30 ctg gta tgt gaa acc tcc ttc aac aaa aaa gaa aaa tca gag atg gtg     144
Leu Val Cys Glu Thr Ser Phe Asn Lys Lys Glu Lys Ser Glu Met Val
         35                  40                  45 cca agt tgc ccc ttt atc tat atc atc cgt aag gat gta gat gtt tac     192
Pro Ser Cys Pro Phe Ile Tyr Ile Ile Arg Lys Asp Val Asp Val Tyr
 50                  55                  60 tct caa atc ttg aga aaa ctc ttc aat gaa tcc cat gga atc ttt ctg     240
Ser Gln Ile Leu Arg Lys Leu Phe Asn Glu Ser His Gly Ile Phe Leu
 65                  70                  75                  80 ggc ctc cag aga att gac gaa gag ttg act gga aaa tcc aga aaa tct     288
Gly Leu Gln Arg Ile Asp Glu Glu Leu Thr Gly Lys Ser Arg Lys Ser
             85                  90                  95 caa ttg gtt cga gtg agt aaa aac tac cga tca gtc atc aga gca tgt     336
Gln Leu Val Arg Val Ser Lys Asn Tyr Arg Ser Val Ile Arg Ala Cys
            100                 105                 110 atg gag gaa atg cac cag gtt gca att gct gct aaa gat cca gcc aat     384
Met Glu Glu Met His Gln Val Ala Ile Ala Ala Lys Asp Pro Ala Asn
            115                 120                 125 ggc cgc cag ttc agc agc cag gtc tcc att ttg tca gca atg gag ctc     432
Gly Arg Gln Phe Ser Ser Gln Val Ser Ile Leu Ser Ala Met Glu Leu
        130                 135                 140 atc tgg aac ctg tgt gag att ctt ttt att gaa gtg gcc cca gct ggc     480
Ile Trp Asn Leu Cys Glu Ile Leu Phe Ile Glu Val Ala Pro Ala Gly
145                 150                 155                 160 cct ctc ctc ctc cat ctc ctt gac tgg gtc cgg ctc cat gtg tgc gag     528
Pro Leu Leu Leu His Leu Leu Asp Trp Val Arg Leu His Val Cys Glu
                165                 170                 175 gtg gac agt ttg tcg gca gat gtt ctg ggc agt gag aat cca agc aaa     576
Val Asp Ser Leu Ser Ala Asp Val Leu Gly Ser Glu Asn Pro Ser Lys
            180                 185                 190 cat gac agc ttc tgg aac ttg gtg acc atc ttg gtg ctg cag ggc cgg     624
His Asp Ser Phe Trp Asn Leu Val Thr Ile Leu Val Leu Gln Gly Arg
        195                 200                 205 ctg gat gag gcc cga cag atg ctc tcc aag gaa gcc gat gcc agc ccc     672
Leu Asp Glu Ala Arg Gln Met Leu Ser Lys Glu Ala Asp Ala Ser Pro
    210                 215                 220 gcc tct gca ggc ata tgc cga atc atg ggg gac ctg atg agg aca atg     720
Ala Ser Ala Gly Ile Cys Arg Ile Met Gly Asp Leu Met Arg Thr Met
225                 230                 235                 240 ccc att ctt agt cct ggg aac acc cag aca ctg aca gag ctg gag ctg     768
Pro Ile Leu Ser Pro Gly Asn Thr Gln Thr Leu Thr Glu Leu Glu Leu
                245                 250                 255 aag tgg cag cac tgg cac gag gaa tgt gag cgg tac ctc cag gac agc     816
Lys Trp Gln His Trp His Glu Glu Cys Glu Arg Tyr Leu Gln Asp Ser
            260                 265                 270 aca ttc gcc acc agc cct cac ctg gag tct ctc ttg aag att atg ctg     864
Thr Phe Ala Thr Ser Pro His Leu Glu Ser Leu Leu Lys Ile Met Leu
        275                 280                 285 gga gac gaa gct gcc ttg tta gag cag aag gaa ctt ctg agt aat tgg     912
Gly Asp Glu Ala Ala Leu Leu Glu Gln Lys Glu Leu Leu Ser Asn Trp
    290                 295                 300 tat cat ttc cta gtg act cgg ctc ttg tac tcc aat ccc aca gta aaa     960
Tyr His Phe Leu Val Thr Arg Leu Leu Tyr Ser Asn Pro Thr Val Lys
305                 310                 315                 320 ccc att gat ctg cac tac tat gcc cag tcc agc ctg gac ctg ttt ctg    1008
```

```
Pro Ile Asp Leu His Tyr Tyr Ala Gln Ser Ser Leu Asp Leu Phe Leu
            325                 330                 335 gga ggt gag agc agc cca gaa ccc ctg gac aac atc ttg ttg gca gcc      1056
Gly Gly Glu Ser Ser Pro Glu Pro Leu Asp Asn Ile Leu Leu Ala Ala
        340                 345                 350 ttt gag ttt gac atc cat caa gta atc aaa gag tgc agc atc gcc ctg      1104
Phe Glu Phe Asp Ile His Gln Val Ile Lys Glu Cys Ser Ile Ala Leu
        355                 360                 365 agc aac tgg tgg ttt gtg gcc cac ctg aca gac ctg ctg gac cac tgc      1152
Ser Asn Trp Trp Phe Val Ala His Leu Thr Asp Leu Leu Asp His Cys
        370                 375                 380 aag ctc ctc cag tca cac aac ctc tat ttc ggt tcc aac atg aga gag      1200
Lys Leu Leu Gln Ser His Asn Leu Tyr Phe Gly Ser Asn Met Arg Glu
385                 390                 395                 400 ttc ctg ctg ctg gag tac gcc tcg gga ctg ttt gct cat ccc agc ctg      1248
Phe Leu Leu Leu Glu Tyr Ala Ser Gly Leu Phe Ala His Pro Ser Leu
                405                 410                 415 tgg cag ctg ggg gtc gat tac ttt gat tac tgc ccc gag ctg ggc cga      1296
Trp Gln Leu Gly Val Asp Tyr Phe Asp Tyr Cys Pro Glu Leu Gly Arg
                420                 425                 430 gtc tcc ctg gag ctg cac att gag cgg ata cct ctg aac acc gag cag      1344
Val Ser Leu Glu Leu His Ile Glu Arg Ile Pro Leu Asn Thr Glu Gln
            435                 440                 445 aaa gcc ctg aag gtg ctg cgg atc tgt gag cag cgg cag atg act gaa      1392
Lys Ala Leu Lys Val Leu Arg Ile Cys Glu Gln Arg Gln Met Thr Glu
        450                 455                 460 caa gtt cgc agc att tgt aag atc tta gcc atg aaa gcc gtc cgc aac      1440
Gln Val Arg Ser Ile Cys Lys Ile Leu Ala Met Lys Ala Val Arg Asn
465                 470                 475                 480 aat cgc ctg ggt tct gcc ctc tct tgg agc atc cgt gct aag gat gcc      1488
Asn Arg Leu Gly Ser Ala Leu Ser Trp Ser Ile Arg Ala Lys Asp Ala
                485                 490                 495 gcc ttt gcc acg ctc gtg tca gac agg ttc ctc agg gat tac tgt gag      1536
Ala Phe Ala Thr Leu Val Ser Asp Arg Phe Leu Arg Asp Tyr Cys Glu
                500                 505                 510 cga ggc tgc ttt tct gat ttg gat ctc att gac aac ctg ggg cca gcc      1584
Arg Gly Cys Phe Ser Asp Leu Asp Leu Ile Asp Asn Leu Gly Pro Ala
            515                 520                 525 atg atg ctc agt gac cga ctg aca ttc ctg gga aag tat cgc gag ttc      1632
Met Met Leu Ser Asp Arg Leu Thr Phe Leu Gly Lys Tyr Arg Glu Phe
        530                 535                 540 cac cgt atg tac ggg gag aag cgt ttt gcc gac gca gct tct ctc ctt      1680
His Arg Met Tyr Gly Glu Lys Arg Phe Ala Asp Ala Ala Ser Leu Leu
545                 550                 555                 560 ctg tcc ttg atg acg tct cgg att gcc cct cgg tct ttc tgg atg act      1728
Leu Ser Leu Met Thr Ser Arg Ile Ala Pro Arg Ser Phe Trp Met Thr
                565                 570                 575 ctg ctg aca gat gcc ttg ccc ctt ttg gaa cag aaa cag gtg att ttc      1776
Leu Leu Thr Asp Ala Leu Pro Leu Leu Glu Gln Lys Gln Val Ile Phe
                580                 585                 590 tca gca gaa cag act tat gag ttg atg cgg tgt ctg gag gac ttg acg      1824
Ser Ala Glu Gln Thr Tyr Glu Leu Met Arg Cys Leu Glu Asp Leu Thr
            595                 600                 605 tca aga aga cct gtg cat gga gaa tct gat acc gag cag ctc cag gat      1872
Ser Arg Arg Pro Val His Gly Glu Ser Asp Thr Glu Gln Leu Gln Asp
        610                 615                 620 gat gac ata gag acc acc aag gtg gaa atg ctg aga ctt tct ctg gca      1920
Asp Asp Ile Glu Thr Thr Lys Val Glu Met Leu Arg Leu Ser Leu Ala
625                 630                 635                 640
```

```
                cga aat ctt gct cgg gca att ata aga gaa ggc tca ctg gaa ggt tcc    1968
                Arg Asn Leu Ala Arg Ala Ile Ile Arg Glu Gly Ser Leu Glu Gly Ser
                                645                 650                 655 tga                                                                                1971
```

<210> SEQ ID NO 2
<211> LENGTH: 656
<212> TYPE: PRT
<213> ORGANISM: Homo sapiens

<400> SEQUENCE: 2

```
Met Glu Glu Leu Asp Gly Glu Pro Thr Val Thr Leu Ile Pro Gly Val
1               5                   10                  15

Asn Ser Lys Lys Asn Gln Met Tyr Phe Asp Trp Gly Pro Gly Glu Met
                20                  25                  30

Leu Val Cys Glu Thr Ser Phe Asn Lys Glu Lys Ser Glu Met Val
            35                  40                  45

Pro Ser Cys Pro Phe Ile Tyr Ile Ile Arg Lys Asp Val Asp Val Tyr
    50                  55                  60

Ser Gln Ile Leu Arg Lys Leu Phe Asn Glu Ser His Gly Ile Phe Leu
65                  70                  75                  80

Gly Leu Gln Arg Ile Asp Glu Glu Leu Thr Gly Lys Ser Arg Lys Ser
                85                  90                  95

Gln Leu Val Arg Val Ser Lys Asn Tyr Arg Ser Val Ile Arg Ala Cys
            100                 105                 110

Met Glu Glu Met His Gln Val Ala Ile Ala Ala Lys Asp Pro Ala Asn
        115                 120                 125

Gly Arg Gln Phe Ser Ser Gln Val Ser Ile Leu Ser Ala Met Glu Leu
    130                 135                 140

Ile Trp Asn Leu Cys Glu Ile Leu Phe Ile Glu Val Ala Pro Ala Gly
145                 150                 155                 160

Pro Leu Leu Leu His Leu Leu Asp Trp Val Arg Leu His Val Cys Glu
                165                 170                 175

Val Asp Ser Leu Ser Ala Asp Val Leu Gly Ser Glu Asn Pro Ser Lys
            180                 185                 190

His Asp Ser Phe Trp Asn Leu Val Thr Ile Leu Val Leu Gln Gly Arg
        195                 200                 205

Leu Asp Glu Ala Arg Gln Met Leu Ser Lys Glu Ala Asp Ala Ser Pro
    210                 215                 220

Ala Ser Ala Gly Ile Cys Arg Ile Met Gly Asp Leu Met Arg Thr Met
225                 230                 235                 240

Pro Ile Leu Ser Pro Gly Asn Thr Gln Thr Leu Thr Glu Leu Glu Leu
                245                 250                 255

Lys Trp Gln His Trp His Glu Glu Cys Glu Arg Tyr Leu Gln Asp Ser
            260                 265                 270

Thr Phe Ala Thr Ser Pro His Leu Glu Ser Leu Leu Lys Ile Met Leu
        275                 280                 285

Gly Asp Glu Ala Ala Leu Leu Glu Gln Lys Glu Leu Leu Ser Asn Trp
    290                 295                 300

Tyr His Phe Leu Val Thr Arg Leu Leu Tyr Ser Asn Pro Thr Val Lys
305                 310                 315                 320

Pro Ile Asp Leu His Tyr Tyr Ala Gln Ser Ser Leu Asp Leu Phe Leu
                325                 330                 335

Gly Gly Glu Ser Ser Pro Glu Pro Leu Asp Asn Ile Leu Leu Ala Ala
            340                 345                 350
```

Phe Glu Phe Asp Ile His Gln Val Ile Lys Glu Cys Ser Ile Ala Leu
        355                 360                 365

Ser Asn Trp Trp Phe Val Ala His Leu Thr Asp Leu Leu Asp His Cys
    370                 375                 380

Lys Leu Leu Gln Ser His Asn Leu Tyr Phe Gly Ser Asn Met Arg Glu
385                 390                 395                 400

Phe Leu Leu Leu Glu Tyr Ala Ser Gly Leu Phe Ala His Pro Ser Leu
                405                 410                 415

Trp Gln Leu Gly Val Asp Tyr Phe Asp Tyr Cys Pro Glu Leu Gly Arg
            420                 425                 430

Val Ser Leu Glu Leu His Ile Glu Arg Ile Pro Leu Asn Thr Glu Gln
        435                 440                 445

Lys Ala Leu Lys Val Leu Arg Ile Cys Glu Gln Arg Gln Met Thr Glu
    450                 455                 460

Gln Val Arg Ser Ile Cys Lys Ile Leu Ala Met Lys Ala Val Arg Asn
465                 470                 475                 480

Asn Arg Leu Gly Ser Ala Leu Ser Trp Ser Ile Arg Ala Lys Asp Ala
                485                 490                 495

Ala Phe Ala Thr Leu Val Ser Asp Arg Phe Leu Arg Asp Tyr Cys Glu
            500                 505                 510

Arg Gly Cys Phe Ser Asp Leu Asp Leu Ile Asp Asn Leu Gly Pro Ala
        515                 520                 525

Met Met Leu Ser Asp Arg Leu Thr Phe Leu Gly Lys Tyr Arg Glu Phe
    530                 535                 540

His Arg Met Tyr Gly Glu Lys Arg Phe Ala Asp Ala Ala Ser Leu Leu
545                 550                 555                 560

Leu Ser Leu Met Thr Ser Arg Ile Ala Pro Arg Ser Phe Trp Met Thr
                565                 570                 575

Leu Leu Thr Asp Ala Leu Pro Leu Leu Glu Gln Lys Gln Val Ile Phe
            580                 585                 590

Ser Ala Glu Gln Thr Tyr Glu Leu Met Arg Cys Leu Glu Asp Leu Thr
        595                 600                 605

Ser Arg Arg Pro Val His Gly Glu Ser Asp Thr Glu Gln Leu Gln Asp
    610                 615                 620

Asp Asp Ile Glu Thr Thr Lys Val Glu Met Leu Arg Leu Ser Leu Ala
625                 630                 635                 640

Arg Asn Leu Ala Arg Ala Ile Ile Arg Glu Gly Ser Leu Glu Gly Ser
                645                 650                 655

<210> SEQ ID NO 3
<211> LENGTH: 2335
<212> TYPE: DNA
<213> ORGANISM: Homo sapiens
<220> FEATURE:
<221> NAME/KEY: CDS
<222> LOCATION: (486)..(1568)

<400> SEQUENCE: 3
tttattctct ggaacatgaa acattctgtt gtgctcatat catgcaaatt atcactagta      60
ggagagcaga gagtggaaat gttccaggta taaagaccca agataaag aagctcagag      120 tcgttagaaa caggagcaga tgtacagggt ttgcctgact cacactcaag gttgcataag      180
caagatttca aaattaatcc tattctggag acctcaaccc aatgtacaat gttcctgact      240
ggaaaagaag aactatattt ttctgatttt tttttcaaa tctttaccat tagttgccct      300

```
gtatctccgc cttcactttc tgcaggaaac tttatttcct acttctgcat gccaagtttc    360
tacctctaga tctgtttggt tcagttgctg agaagcctga cataccagga ctgcctgaga    420
caagccacaa gctgaacaga gaaagtggat tgaacaagga cgcatttccc cagtacatcc    480 acaac atg ctg tcc aca tct cgt tct cgg ttt atc aga aat acc aac gag    530
      Met Leu Ser Thr Ser Arg Ser Arg Phe Ile Arg Asn Thr Asn Glu
      1               5                   10                  15 agc ggt gaa gaa gtc acc acc ttt ttt gat tat gat tac ggt gct ccc      578
Ser Gly Glu Glu Val Thr Thr Phe Phe Asp Tyr Asp Tyr Gly Ala Pro
                20                  25                  30 tgt cat aaa ttt gac gtg aag caa att ggg gcc caa ctc ctg cct ccg      626
Cys His Lys Phe Asp Val Lys Gln Ile Gly Ala Gln Leu Leu Pro Pro
            35                  40                  45 ctc tac tcg ctg gtg ttc atc ttt ggt ttt gtg ggc aac atg ctg gtc      674
Leu Tyr Ser Leu Val Phe Ile Phe Gly Phe Val Gly Asn Met Leu Val
        50                  55                  60 gtc ctc atc tta ata aac tgc aaa aag ctg aag tgc ttg act gac att      722
Val Leu Ile Leu Ile Asn Cys Lys Lys Leu Lys Cys Leu Thr Asp Ile
    65                  70                  75 tac ctg ctc aac ctg gcc atc tct gat ctg ctt ttt ctt att act ctc      770
Tyr Leu Leu Asn Leu Ala Ile Ser Asp Leu Leu Phe Leu Ile Thr Leu
80                  85                  90                  95 cca ttg tgg gct cac tct gct gca aat gag tgg gtc ttt ggg aat gca      818
Pro Leu Trp Ala His Ser Ala Ala Asn Glu Trp Val Phe Gly Asn Ala
                100                 105                 110 atg tgc aaa tta ttc aca ggg ctg tat cac atc ggt tat ttt ggc gga      866
Met Cys Lys Leu Phe Thr Gly Leu Tyr His Ile Gly Tyr Phe Gly Gly
            115                 120                 125 atc ttc ttc atc atc ctc ctg aca atc gat aga tac ctg gct att gtc      914
Ile Phe Phe Ile Ile Leu Leu Thr Ile Asp Arg Tyr Leu Ala Ile Val
        130                 135                 140 cat gct gtg ttt gct tta aaa gcc agg acg gtc acc ttt ggg gtg gtg      962
His Ala Val Phe Ala Leu Lys Ala Arg Thr Val Thr Phe Gly Val Val
    145                 150                 155 aca agt gtg atc acc tgg ttg gtg gct gtg ttt gct tct gtc cca gga      1010
Thr Ser Val Ile Thr Trp Leu Val Ala Val Phe Ala Ser Val Pro Gly
160                 165                 170                 175 atc atc ttt act aaa tgc cag aaa gaa gat tct gtt tat gtc tgt ggc      1058
Ile Ile Phe Thr Lys Cys Gln Lys Glu Asp Ser Val Tyr Val Cys Gly
                180                 185                 190 cct tat ttt cca cga gga tgg aat aat ttc cac aca ata atg agg aac      1106
Pro Tyr Phe Pro Arg Gly Trp Asn Asn Phe His Thr Ile Met Arg Asn
            195                 200                 205 att ttg ggg ctg gtc ctg ccg ctc ctc atc atg gtc atc tgc tac tcg      1154
Ile Leu Gly Leu Val Leu Pro Leu Leu Ile Met Val Ile Cys Tyr Ser
        210                 215                 220 gga atc ctg aaa acc ctg ctt cgg tgt cga aac gag aag aag agg cat      1202
Gly Ile Leu Lys Thr Leu Leu Arg Cys Arg Asn Glu Lys Lys Arg His
    225                 230                 235 agg gca gtg aga gtc atc ttc acc atc atg att gtt tac ttt ctc ttc      1250
Arg Ala Val Arg Val Ile Phe Thr Ile Met Ile Val Tyr Phe Leu Phe
240                 245                 250                 255 tgg act ccc tat aat att gtc att ctc ctg aac acc ttc cag gaa ttc      1298
Trp Thr Pro Tyr Asn Ile Val Ile Leu Leu Asn Thr Phe Gln Glu Phe
                260                 265                 270 ttc ggc ctg agt aac tgt gaa agc acc agt caa ctg gac caa gcc acg      1346
Phe Gly Leu Ser Asn Cys Glu Ser Thr Ser Gln Leu Asp Gln Ala Thr
            275                 280                 285 cag gtg aca gag act ctt ggg atg act cac tgc tgc atc aat ccc atc      1394
```

```
                Gln Val Thr Glu Thr Leu Gly Met Thr His Cys Cys Ile Asn Pro Ile
                            290                 295                 300 atc tat gcc ttc gtt ggg gag aag ttc aga agg tat ctc tcg gtg ttc      1442
Ile Tyr Ala Phe Val Gly Glu Lys Phe Arg Arg Tyr Leu Ser Val Phe
305                 310                 315 ttc cga aag cac atc acc aag cgc ttc tgc aaa caa tgt cca gtt ttc      1490
Phe Arg Lys His Ile Thr Lys Arg Phe Cys Lys Gln Cys Pro Val Phe
320                 325                 330                 335 tac agg gag aca gtg gat gga gtg act tca aca aac acg cct tcc act      1538
Tyr Arg Glu Thr Val Asp Gly Val Thr Ser Thr Asn Thr Pro Ser Thr
                    340                 345                 350 ggg gag cag gaa gtc tcg gct ggt tta taa aacgaggagc agtttgattg         1588
Gly Glu Gln Glu Val Ser Ala Gly Leu
                355                 360 ttgtttataa agggagataa caatctgtat ataacaacaa acttcaaggg tttgttgaac    1648
aatagaaacc tgtaaagcag gtgcccagga acctcagggc tgtgtgtact aatacagact    1708
atgtcaccca atgcatatcc aacatgtgct cagggaataa tccagaaaaa ctgtgggtag    1768
agactttgac tctccagaaa gctcatctca gctcctgaaa aatgcctcat taccttgtgc    1828
taatcctctt tttctagtct tcataatttc ttcactcaat ctctgattct gtcaatgtct    1888
tgaaatcaag ggccagctgg aggtgaagaa gagaatgtga caggcacaga tgaatgggag    1948 tgagggatg  tgggggtcagg gctgagagga aaggagggga  gacatgagca tggctgagcc   2008
tggacaaaga caaaggtgag caaagggctc acgcattcag ccaggagatg atactggtcc    2068
ttagccccat ctgccacgtg tatttaacct tgaagggttc accaggtcag ggagagtttg    2128
ggaactgcaa taacctggga gttttggtgg agtccgatga ttctcttttg cataagtgca    2188
tgacatattt ttgctttatt acagtttatc tatggcaccc atgcacctta catttgaaat    2248
ctatgaaata tcatgctcca ttgttcagat gcttcttagg ccacatcccc ctgtctaaaa    2308
attcagaaaa ttttgtttta taaaaga                                         2335

<210> SEQ ID NO 4
<211> LENGTH: 360
<212> TYPE: PRT
<213> ORGANISM: Homo sapiens

<400> SEQUENCE: 4

Met Leu Ser Thr Ser Arg Ser Arg Phe Ile Arg Asn Thr Asn Glu Ser
1               5                   10                  15

Gly Glu Glu Val Thr Thr Phe Phe Asp Tyr Asp Tyr Gly Ala Pro Cys
                20                  25                  30

His Lys Phe Asp Val Lys Gln Ile Gly Ala Gln Leu Leu Pro Pro Leu
            35                  40                  45

Tyr Ser Leu Val Phe Ile Phe Gly Phe Val Gly Asn Met Leu Val Val
        50                  55                  60

Leu Ile Leu Ile Asn Cys Lys Lys Leu Lys Cys Leu Thr Asp Ile Tyr
65                  70                  75                  80

Leu Leu Asn Leu Ala Ile Ser Asp Leu Leu Phe Leu Ile Thr Leu Pro
                85                  90                  95

Leu Trp Ala His Ser Ala Ala Asn Glu Trp Val Phe Gly Asn Ala Met
            100                 105                 110

Cys Lys Leu Phe Thr Gly Leu Tyr His Ile Gly Tyr Phe Gly Gly Ile
        115                 120                 125

Phe Phe Ile Ile Leu Leu Thr Ile Asp Arg Tyr Leu Ala Ile Val His
    130                 135                 140
```

Ala Val Phe Ala Leu Lys Ala Arg Thr Val Thr Phe Gly Val Val Thr
145                 150                 155                 160

Ser Val Ile Thr Trp Leu Val Ala Val Phe Ala Ser Val Pro Gly Ile
                165                 170                 175

Ile Phe Thr Lys Cys Gln Lys Glu Asp Ser Val Tyr Val Cys Gly Pro
            180                 185                 190

Tyr Phe Pro Arg Gly Trp Asn Asn Phe His Thr Ile Met Arg Asn Ile
        195                 200                 205

Leu Gly Leu Val Leu Pro Leu Leu Ile Met Val Ile Cys Tyr Ser Gly
    210                 215                 220

Ile Leu Lys Thr Leu Leu Arg Cys Arg Asn Glu Lys Lys Arg His Arg
225                 230                 235                 240

Ala Val Arg Val Ile Phe Thr Ile Met Ile Val Tyr Phe Leu Phe Trp
                245                 250                 255

Thr Pro Tyr Asn Ile Val Ile Leu Leu Asn Thr Phe Gln Glu Phe Phe
            260                 265                 270

Gly Leu Ser Asn Cys Glu Ser Thr Ser Gln Leu Asp Gln Ala Thr Gln
        275                 280                 285

Val Thr Glu Thr Leu Gly Met Thr His Cys Cys Ile Asn Pro Ile Ile
    290                 295                 300

Tyr Ala Phe Val Gly Glu Lys Phe Arg Arg Tyr Leu Ser Val Phe Phe
305                 310                 315                 320

Arg Lys His Ile Thr Lys Arg Phe Cys Lys Gln Cys Pro Val Phe Tyr
                325                 330                 335

Arg Glu Thr Val Asp Gly Val Thr Ser Thr Asn Thr Pro Ser Thr Gly
            340                 345                 350

Glu Gln Glu Val Ser Ala Gly Leu
        355                 360

<210> SEQ ID NO 5
<211> LENGTH: 3686
<212> TYPE: DNA
<213> ORGANISM: Homo sapiens
<220> FEATURE:
<221> NAME/KEY: CDS
<222> LOCATION: (358)..(1416)

<400> SEQUENCE: 5
cttcagatag attatatctg gagtgaagaa tcctgccacc tatgtatctg catagtatt      60 ctgtgtagtg ggatgagcag agaacaaaaa caaaataatc cagtgagaaa agcccgtaaa     120
taaaccttca gaccagagat ctattctcta gcttatttta agctcaactt aaaaagaaga     180
actgttctct gattcttttc gccttcaata cacttaatga tttaactcca ccctccttca     240
aaagaaacag catttcctac ttttatactg tctatatgat tgatttgcac agctcatctg     300
gccagaagag ctgagacatc cgttccccta caagaaactc tccccgggtg aacaag         357 atg gat tat caa gtg tca agt cca atc tat gac atc aat tat tat aca     405
Met Asp Tyr Gln Val Ser Ser Pro Ile Tyr Asp Ile Asn Tyr Tyr Thr
1               5                   10                  15 tcg gag ccc tgc caa aaa atc aat gtg aag caa atc gca gcc cgc ctc     453
Ser Glu Pro Cys Gln Lys Ile Asn Val Lys Gln Ile Ala Ala Arg Leu
                20                  25                  30 ctg cct ccg ctc tac tca ctg gtg ttc atc ttt ggt ttt gtg ggc aac     501
Leu Pro Pro Leu Tyr Ser Leu Val Phe Ile Phe Gly Phe Val Gly Asn
            35                  40                  45 atg ctg gtc atc ctc atc ctg ata aac tgc aaa agg ctg aag agc atg     549

```
                Met Leu Val Ile Leu Ile Leu Ile Asn Cys Lys Arg Leu Lys Ser Met
                    50                  55                  60 act gac atc tac ctg ctc aac ctg gcc atc tct gac ctg ttt ttc ctt            597
Thr Asp Ile Tyr Leu Leu Asn Leu Ala Ile Ser Asp Leu Phe Phe Leu
65                  70                  75                  80 ctt act gtc ccc ttc tgg gct cac tat gct gcc gcc cag tgg gac ttt            645
Leu Thr Val Pro Phe Trp Ala His Tyr Ala Ala Ala Gln Trp Asp Phe
                    85                  90                  95 gga aat aca atg tgt caa ctc ttg aca ggg ctc tat ttt ata ggc ttc            693
Gly Asn Thr Met Cys Gln Leu Leu Thr Gly Leu Tyr Phe Ile Gly Phe
                100                 105                 110 ttc tct gga atc ttc ttc atc atc ctc ctg aca atc gat agg tac ctg            741
Phe Ser Gly Ile Phe Phe Ile Ile Leu Leu Thr Ile Asp Arg Tyr Leu
                115                 120                 125 gct gtc gtc cat gct gtg ttt gct tta aaa gcc agg acg gtc acc ttt            789
Ala Val Val His Ala Val Phe Ala Leu Lys Ala Arg Thr Val Thr Phe
            130                 135                 140 ggg gtg gtg aca agt gtg atc act tgg gtg gtg gct gtg ttt gcg tct            837
Gly Val Val Thr Ser Val Ile Thr Trp Val Val Ala Val Phe Ala Ser
145                 150                 155                 160 ctc cca gga atc atc ttt acc aga tct caa aaa gaa ggt ctt cat tac            885
Leu Pro Gly Ile Ile Phe Thr Arg Ser Gln Lys Glu Gly Leu His Tyr
                165                 170                 175 acc tgc agc tct cat ttt cca tac agt cag tat caa ttc tgg aag aat            933
Thr Cys Ser Ser His Phe Pro Tyr Ser Gln Tyr Gln Phe Trp Lys Asn
                180                 185                 190 ttc cag aca tta aag ata gtc atc ttg ggg ctg gtc ctg ccg ctg ctt            981
Phe Gln Thr Leu Lys Ile Val Ile Leu Gly Leu Val Leu Pro Leu Leu
                195                 200                 205 gtc atg gtc atc tgc tac tcg gga atc cta aaa act ctg ctt cgg tgt           1029
Val Met Val Ile Cys Tyr Ser Gly Ile Leu Lys Thr Leu Leu Arg Cys
            210                 215                 220 cga aat gag aag aag agg cac agg gct gtg agg ctt atc ttc acc atc           1077
Arg Asn Glu Lys Lys Arg His Arg Ala Val Arg Leu Ile Phe Thr Ile
225                 230                 235                 240 atg att gtt tat ttt ctc ttc tgg gct ccc tac aac att gtc ctt ctc           1125
Met Ile Val Tyr Phe Leu Phe Trp Ala Pro Tyr Asn Ile Val Leu Leu
                245                 250                 255 ctg aac acc ttc cag gaa ttc ttt ggc ctg aat aat tgc agt agc tct           1173
Leu Asn Thr Phe Gln Glu Phe Phe Gly Leu Asn Asn Cys Ser Ser Ser
                260                 265                 270 aac agg ttg gac caa gct atg cag gtg aca gag act ctt ggg atg acg           1221
Asn Arg Leu Asp Gln Ala Met Gln Val Thr Glu Thr Leu Gly Met Thr
            275                 280                 285 cac tgc tgc atc aac ccc atc atc tat gcc ttt gtc ggg gag aag ttc           1269
His Cys Cys Ile Asn Pro Ile Ile Tyr Ala Phe Val Gly Glu Lys Phe
            290                 295                 300 aga aac tac ctc tta gtc ttc ttc caa aag cac att gcc aaa cgc ttc           1317
Arg Asn Tyr Leu Leu Val Phe Phe Gln Lys His Ile Ala Lys Arg Phe
305                 310                 315                 320 tgc aaa tgc tgt tct att ttc cag caa gag gct ccc gag cga gca agc           1365
Cys Lys Cys Cys Ser Ile Phe Gln Gln Glu Ala Pro Glu Arg Ala Ser
                325                 330                 335 tca gtt tac acc cga tcc act ggg gag cag gaa ata tct gtg ggc ttg           1413
Ser Val Tyr Thr Arg Ser Thr Gly Glu Gln Glu Ile Ser Val Gly Leu
                340                 345                 350 tga cacggactca agtgggctgg tgacccagtc agagttgtgc acatggctta                1466
gttttcatac acagcctggg ctgggggtgg ggtgggagag gtctttttta aaggaagtt          1526
```

```
actgttatag agggtctaag attcatccat ttatttggca tctgtttaaa gtagattaga    1586
tcttttaagc ccatcaatta tagaaagcca aatcaaaata tgttgatgaa aaatagcaac    1646 cttttatct cccccttcaca tgcatcaagt tattgacaaa ctctcccttc actccgaaag    1706
ttccttatgt atatttaaaa gaaagcctca gagaattgct gattcttgag tttagtgatc    1766
tgaacagaaa taccaaaatt atttcagaaa tgtacaactt tttacctagt acaaggcaac    1826 ataggttg taaatgtgtt taaaacaggt ctttgtcttg ctatggggag aaaagacatg       1886
aatatgatta gtaaagaaat gacactttc atgtgtgatt tcccctccaa ggtatggtta     1946
ataagtttca ctgacttaga accaggcgag agacttgtgg cctgggagag ctggggaagc    2006
ttcttaaatg agaaggaatt tgagttggat catctattgc tggcaaagac agaagcctca    2066
ctgcaagcac tgcatgggca agcttggctg tagaaggaga cagagctggt tgggaagaca    2126
tggggaggaa ggacaaggct agatcatgaa gaaccttgac ggcattgctc cgtctaagtc    2186
atgagctgag cagggagatc ctggttggtg ttgcagaagg tttactctgt ggccaaagga    2246
gggtcaggaa ggatgagcat ttagggcaag agaccacca acagccctca ggtcagggtg     2306
aggatggcct ctgctaagct caaggcgtga ggatgggaag gagggaggta ttcgtaagga    2366
tgggaaggag ggaggtattc gtgcagcata tgaggatgca gagtcagcag aactggggtg    2426
gatttgggtt ggaagtgagg gtcagagagg agtcagagag aatccctagt cttcaagcag    2486
attggagaaa cccttgaaaa gacatcaagc acagaaggag gaggaggagg tttaggtcaa    2546
gaagaagatg gattggtgta aaaggatggg tctggtttgc agagcttgaa cacagtctca    2606
cccagactcc aggctgtctt tcactgaatg cttctgactt catagatttc cttcccatcc    2666
cagctgaaat actgaggggt ctccaggagg agactagatt tatgaataca cgaggtatga    2726
ggtctaggaa catacttcag ctcacacatg agatctaggt gaggattgat tacctagtag    2786
tcatttcatg ggttgttggg aggattctat gaggcaacca caggcagcat ttagcacata    2846
ctacacattc aataagcatc aaactcttag ttactcattc agggatagca ctgagcaaag    2906
cattgagcaa aggggtccca tagaggtgag ggaagcctga aaaactaaga tgctgcctgc    2966
ccagtgcaca caagtgtagg tatcattttc tgcatttaac cgtcaatagg caaagggggg    3026
aagggacata ttcatttgga aataagctgc cttgagcctt aaaacccaca aaagtacaat    3086
ttaccagcct ccgtatttca gactgaatgg gggtggggg ggcgccttag gtacttattc     3146
cagatgcctt ctccagacaa accagaagca acagaaaaaa tcgtctctcc ctcccttta     3206 aatgaatata cccctagtg tttgggtata ttcatttcaa agggagagag agaggttttt     3266
ttctgttctg tctcatatga ttgtgcacat acttgagact gttttgaatt tgggggatgg    3326
ctaaaaccat catagtacag gtaaggtgag ggaatagtaa gtggtgagaa ctactcaggg    3386
aatgaaggtg tcagaataat aagaggtgct actgactttc tcagcctctg aatatgaacg    3446
gtgagcattg tggctgtcag caggaagcaa cgaagggaaa tgtctttcct tttgctctta    3506
agttgtggag agtgcaacag tagcataggg ccctaccctc tgggccaagt caaagacatt    3566
ctgacatctt agtatttgca tattcttatg tatgtgaaag ttacaaattg cttgaaagaa    3626
aatatgcatc taataaaaaa caccttctaa aataaaaaaa aaaaaaaaaa aaaaaaaaa     3686
```

<210> SEQ ID NO 6
<211> LENGTH: 352
<212> TYPE: PRT
<213> ORGANISM: Homo sapiens

<400> SEQUENCE: 6

```
Met Asp Tyr Gln Val Ser Ser Pro Ile Tyr Asp Ile Asn Tyr Tyr Thr
1               5                   10                  15

Ser Glu Pro Cys Gln Lys Ile Asn Val Lys Gln Ile Ala Ala Arg Leu
            20                  25                  30

Leu Pro Pro Leu Tyr Ser Leu Val Phe Ile Phe Gly Phe Val Gly Asn
        35                  40                  45

Met Leu Val Ile Leu Ile Leu Ile Asn Cys Lys Arg Leu Lys Ser Met
50                  55                  60

Thr Asp Ile Tyr Leu Leu Asn Leu Ala Ile Ser Asp Leu Phe Phe Leu
65                  70                  75                  80

Leu Thr Val Pro Phe Trp Ala His Tyr Ala Ala Ala Gln Trp Asp Phe
                85                  90                  95

Gly Asn Thr Met Cys Gln Leu Leu Thr Gly Leu Tyr Phe Ile Gly Phe
                100                 105                 110

Phe Ser Gly Ile Phe Phe Ile Ile Leu Leu Thr Ile Asp Arg Tyr Leu
        115                 120                 125

Ala Val Val His Ala Val Phe Ala Leu Lys Ala Arg Thr Val Thr Phe
130                 135                 140

Gly Val Val Thr Ser Val Ile Thr Trp Val Val Ala Val Phe Ala Ser
145                 150                 155                 160

Leu Pro Gly Ile Ile Phe Thr Arg Ser Gln Lys Glu Gly Leu His Tyr
                165                 170                 175

Thr Cys Ser Ser His Phe Pro Tyr Ser Gln Tyr Gln Phe Trp Lys Asn
                180                 185                 190

Phe Gln Thr Leu Lys Ile Val Ile Leu Gly Leu Val Leu Pro Leu Leu
        195                 200                 205

Val Met Val Ile Cys Tyr Ser Gly Ile Leu Lys Thr Leu Leu Arg Cys
210                 215                 220

Arg Asn Glu Lys Lys Arg His Arg Ala Val Arg Leu Ile Phe Thr Ile
225                 230                 235                 240

Met Ile Val Tyr Phe Leu Phe Trp Ala Pro Tyr Asn Ile Val Leu Leu
                245                 250                 255

Leu Asn Thr Phe Gln Glu Phe Phe Gly Leu Asn Asn Cys Ser Ser Ser
                260                 265                 270

Asn Arg Leu Asp Gln Ala Met Gln Val Thr Glu Thr Leu Gly Met Thr
        275                 280                 285

His Cys Cys Ile Asn Pro Ile Ile Tyr Ala Phe Val Gly Glu Lys Phe
290                 295                 300

Arg Asn Tyr Leu Leu Val Phe Phe Gln Lys His Ile Ala Lys Arg Phe
305                 310                 315                 320

Cys Lys Cys Cys Ser Ile Phe Gln Gln Glu Ala Pro Glu Arg Ala Ser
                325                 330                 335

Ser Val Tyr Thr Arg Ser Thr Gly Glu Gln Glu Ile Ser Val Gly Leu
                340                 345                 350
```

<210> SEQ ID NO 7
<211> LENGTH: 760
<212> TYPE: DNA
<213> ORGANISM: Homo sapiens
<220> FEATURE:
<221> NAME/KEY: CDS
<222> LOCATION: (74)..(373)

<400> SEQUENCE: 7
gaggaaccga gaggctgaga ctaacccaga aacatccaat tctcaaactg aagctcgcac    60

```
tctcgcctcc agc atg aaa gtc tct gcc gcc ctt ctg tgc ctg ctg ctc      109
            Met Lys Val Ser Ala Ala Leu Leu Cys Leu Leu Leu
            1               5                   10 ata gca gcc acc ttc att ccc caa ggg ctc gct cag cca gat gca atc      157
Ile Ala Ala Thr Phe Ile Pro Gln Gly Leu Ala Gln Pro Asp Ala Ile
        15                  20                  25 aat gcc cca gtc acc tgc tgt tat aac ttc acc aat agg aag atc tca      205
Asn Ala Pro Val Thr Cys Cys Tyr Asn Phe Thr Asn Arg Lys Ile Ser
30                  35                  40 gtg cag agg ctc gcg agc tat aga aga atc acc agc agc aag tgt ccc      253
Val Gln Arg Leu Ala Ser Tyr Arg Arg Ile Thr Ser Ser Lys Cys Pro
45                  50                  55                  60 aaa gaa gct gtg atc ttc aag acc att gtg gcc aag gag atc tgt gct      301
Lys Glu Ala Val Ile Phe Lys Thr Ile Val Ala Lys Glu Ile Cys Ala
                65                  70                  75 gac ccc aag cag aag tgg gtt cag gat tcc atg gac cac ctg gac aag      349
Asp Pro Lys Gln Lys Trp Val Gln Asp Ser Met Asp His Leu Asp Lys
            80                  85                  90 caa acc caa act ccg aag act tga acactcactc cacaacccaa gaatctgcag     403
Gln Thr Gln Thr Pro Lys Thr
                95 ctaacttatt ttcccctagc tttccccaga caccctgttt tattttatta taatgaattt     463 tgtttgttga tgtgaaacat tatgccttaa gtaatgttaa ttcttattta agttattgat     523 gttttaagtt tatctttcat ggtactagtg ttttttagat acagagactt ggggaaattg     583 cttttcctct tgaaccacag ttctaccect gggatgtttt gagggtcttt gcaagaatca     643 ttaatacaaa gaatttttt taacattcca atgcattgct aaaatattat tgtggaaatg     703 aatattttgt aactattaca ccaaataaat atatttttgt acaaaaaaaa aaaaaaa       760
```

<210> SEQ ID NO 8
<211> LENGTH: 99
<212> TYPE: PRT
<213> ORGANISM: Homo sapiens

<400> SEQUENCE: 8

```
Met Lys Val Ser Ala Ala Leu Leu Cys Leu Leu Leu Ile Ala Ala Thr
1               5                   10                  15

Phe Ile Pro Gln Gly Leu Ala Gln Pro Asp Ala Ile Asn Ala Pro Val
            20                  25                  30

Thr Cys Cys Tyr Asn Phe Thr Asn Arg Lys Ile Ser Val Gln Arg Leu
        35                  40                  45

Ala Ser Tyr Arg Arg Ile Thr Ser Ser Lys Cys Pro Lys Glu Ala Val
    50                  55                  60

Ile Phe Lys Thr Ile Val Ala Lys Glu Ile Cys Ala Asp Pro Lys Gln
65                  70                  75                  80

Lys Trp Val Gln Asp Ser Met Asp His Leu Asp Lys Gln Thr Gln Thr
                85                  90                  95

Pro Lys Thr
```

<210> SEQ ID NO 9
<211> LENGTH: 1237
<212> TYPE: DNA
<213> ORGANISM: Homo sapiens
<220> FEATURE:
<221> NAME/KEY: CDS
<222> LOCATION: (69)..(344)

<400> SEQUENCE: 9

```
gctgcagagg attcctgcag aggatcaaga cagcacgtgg acctcgcaca gcctctccca      60 caggtacc atg aag gtc tcc gcg gca gcc ctc gct gtc atc ctc att gct     110
         Met Lys Val Ser Ala Ala Ala Leu Ala Val Ile Leu Ile Ala
         1               5                   10 act gcc ctc tgc gct cct gca tct gcc tcc cca tat tcc tcg gac acc     158
Thr Ala Leu Cys Ala Pro Ala Ser Ala Ser Pro Tyr Ser Ser Asp Thr
15                  20                  25                  30 aca ccc tgc tgc ttt gcc tac att gcc cgc cca ctg ccc cgt gcc cac     206
Thr Pro Cys Cys Phe Ala Tyr Ile Ala Arg Pro Leu Pro Arg Ala His
                35                  40                  45 atc aag gag tat ttc tac acc agt ggc aag tgc tcc aac cca gca gtc     254
Ile Lys Glu Tyr Phe Tyr Thr Ser Gly Lys Cys Ser Asn Pro Ala Val
            50                  55                  60 gtc ttt gtc acc cga aag aac cgc caa gtg tgt gcc aac cca gag aag     302
Val Phe Val Thr Arg Lys Asn Arg Gln Val Cys Ala Asn Pro Glu Lys
        65                  70                  75 aaa tgg gtt cgg gag tac atc aac tct ttg gag atg agc tag             344
Lys Trp Val Arg Glu Tyr Ile Asn Ser Leu Glu Met Ser
80                  85                  90 gatggagagt ccttgaacct gaacttacac aaatttgcct gtttctgctt gctcttgtcc    404
tagcttggga ggcttcccct cactatccta ccccacccgc tccttgaagg gcccagattc    464
taccacacag cagcagttac aaaaaccttc cccaggctgg acgtggtggc tcacgcctgt    524
aatcccagca ctttgggagg ccaaggtggg tggatcactt gaggtcagga gttcgagacc    584
agcctggcca acatgatgaa acccatctc tactaaaaat acaaaaaatt agccgggcgt     644
ggtagcgggc gcctgtagtc ccagctactc gggaggctga ggcaggagaa tggcgtgaac    704
ccgggaggcg gagcttgcag tgagccgaga tcgcgccact gcactccagc ctgggcgaca    764
gagcgagact ccgtctcaaa aaaaaaaaa aaaaaaaaa tacaaaaatt agccgggcgt      824
ggtggcccac gcctgtaatc ccagctactc gggaggctaa ggcaggaaaa ttgtttgaac    884
ccaggaggtg gaggctgcag tgagctgaga ttgtgccact tcactccagc ctgggtgaca    944
aagtgagact ccgtcacaac aacaacaaca aaaagcttcc ccaactaaag cctagaagag   1004
cttctgaggc gctgctttgt caaaaggaag tctctaggtt ctgagctctg gctttgcctt   1064
ggctttgcca gggctctgtg accaggaagg aagtcagcat gcctctagag gcaaggaggg   1124
gaggaacact gcactcttaa gcttccgccg tctcaacccc tcacaggagc ttactggcaa   1184
acatgaaaaa tcggcttacc attaaagttc tcaatgcaac cataaaaaaa aaa          1237

<210> SEQ ID NO 10
<211> LENGTH: 91
<212> TYPE: PRT
<213> ORGANISM: Homo sapiens

<400> SEQUENCE: 10

Met Lys Val Ser Ala Ala Ala Leu Ala Val Ile Leu Ile Ala Thr Ala
1               5                   10                  15

Leu Cys Ala Pro Ala Ser Ala Ser Pro Tyr Ser Ser Asp Thr Thr Pro
            20                  25                  30

Cys Cys Phe Ala Tyr Ile Ala Arg Pro Leu Pro Arg Ala His Ile Lys
        35                  40                  45

Glu Tyr Phe Tyr Thr Ser Gly Lys Cys Ser Asn Pro Ala Val Val Phe
    50                  55                  60

Val Thr Arg Lys Asn Arg Gln Val Cys Ala Asn Pro Glu Lys Lys Trp
65                  70                  75                  80
```

Val Arg Glu Tyr Ile Asn Ser Leu Glu Met Ser
            85                  90

<210> SEQ ID NO 11
<211> LENGTH: 21
<212> TYPE: DNA
<213> ORGANISM: Artificial Sequence
<220> FEATURE:
<223> OTHER INFORMATION: primer, FROUNT sense

<400> SEQUENCE: 11
gctgctaaag atccagccaa t                                              21

<210> SEQ ID NO 12
<211> LENGTH: 20
<212> TYPE: DNA
<213> ORGANISM: Artificial Sequence
<220> FEATURE:
<223> OTHER INFORMATION: primer, FROUNT antisense

<400> SEQUENCE: 12
gatgagctcc attgctgaca                                                20

<210> SEQ ID NO 13
<211> LENGTH: 20
<212> TYPE: DNA
<213> ORGANISM: Artificial Sequence
<220> FEATURE:
<223> OTHER INFORMATION: primer, CCR2 sense

<400> SEQUENCE: 13
tgagacaagc cacaagctga                                                20

<210> SEQ ID NO 14
<211> LENGTH: 23
<212> TYPE: DNA
<213> ORGANISM: Artificial Sequence
<220> FEATURE:
<223> OTHER INFORMATION: primer, CCR2 antisense

<400> SEQUENCE: 14
ttctgataaa ccgagaacga gat                                            23

<210> SEQ ID NO 15
<211> LENGTH: 20
<212> TYPE: DNA
<213> ORGANISM: Artificial Sequence
<220> FEATURE:
<223> OTHER INFORMATION: primer, CCR5 sense

<400> SEQUENCE: 15
ctaagctcaa ggcgtgagga                                                20

<210> SEQ ID NO 16
<211> LENGTH: 20
<212> TYPE: DNA
<213> ORGANISM: Artificial Sequence
<220> FEATURE:
<223> OTHER INFORMATION: primer, CCR5 antisense

<400> SEQUENCE: 16
cacttccaac ccaaatccac                                                20

<210> SEQ ID NO 17
<211> LENGTH: 19

```
<212> TYPE: DNA
<213> ORGANISM: Artificial Sequence
<220> FEATURE:
<223> OTHER INFORMATION: primer, CCL2 sense

<400> SEQUENCE: 17
ttctgtgcct gctgctcat                                              19

<210> SEQ ID NO 18
<211> LENGTH: 18
<212> TYPE: DNA
<213> ORGANISM: Artificial Sequence
<220> FEATURE:
<223> OTHER INFORMATION: primer, CCL2 antisense

<400> SEQUENCE: 18
ggggcattga ttgcatct                                               18

<210> SEQ ID NO 19
<211> LENGTH: 20
<212> TYPE: DNA
<213> ORGANISM: Artificial Sequence
<220> FEATURE:
<223> OTHER INFORMATION: primer, CCL5 sense

<400> SEQUENCE: 19
cctcattgct actgccctct                                             20

<210> SEQ ID NO 20
<211> LENGTH: 20
<212> TYPE: DNA
<213> ORGANISM: Artificial Sequence
<220> FEATURE:
<223> OTHER INFORMATION: primer, CCL5 antisense

<400> SEQUENCE: 20
ggtgtggtgt ccgaggaata                                             20

<210> SEQ ID NO 21
<211> LENGTH: 19
<212> TYPE: DNA
<213> ORGANISM: Artificial Sequence
<220> FEATURE:
<223> OTHER INFORMATION: primer, GAPDH sense

<400> SEQUENCE: 21
gaaggtgaag gtcggagtc                                              19

<210> SEQ ID NO 22
<211> LENGTH: 20
<212> TYPE: DNA
<213> ORGANISM: Artificial Sequence
<220> FEATURE:
<223> OTHER INFORMATION: primer, GAPDH antisense

<400> SEQUENCE: 22
gaagatggtg atgggatttc                                             20
```